United States Patent
Noerholm et al.

(10) Patent No.: US 12,018,334 B2
(45) Date of Patent: *Jun. 25, 2024

(54) CONTROLS FOR NUCLEIC ACID ASSAYS

(71) Applicant: Exosome Diagnostics, Inc., Waltham, MA (US)

(72) Inventors: Mikkel Noerholm, Gauting (DE); Susan Belzer, St. Louis Park, MN (US); Charlotte Romain, St. Louis Park, MN (US); Johan Karl Olov Skog, Charlestown, MA (US); Leileata M. Russo, New York, NY (US); Wayne Comper, New York, NY (US)

(73) Assignee: Exosome Diagnostics, Inc., Waltham, MA (US)

( * ) Notice: Subject to any disclaimer, the term of this patent is extended or adjusted under 35 U.S.C. 154(b) by 37 days.

This patent is subject to a terminal disclaimer.

(21) Appl. No.: 17/411,606

(22) Filed: Aug. 25, 2021

(65) Prior Publication Data

US 2021/0388453 A1  Dec. 16, 2021

Related U.S. Application Data

(63) Continuation of application No. 14/424,694, filed as application No. PCT/US2013/057506 on Aug. 30, 2013, now Pat. No. 11,136,627.

(60) Provisional application No. 61/695,116, filed on Aug. 30, 2012.

(51) Int. Cl.
| | | |
|---|---|---|
| C12P 19/34 | (2006.01) | |
| C12N 7/00 | (2006.01) | |
| C12Q 1/6886 | (2018.01) | |

(52) U.S. Cl.
CPC .............. C12Q 1/6886 (2013.01); C12N 7/00 (2013.01); *C12N 2795/18122* (2013.01); *C12N 2795/18131* (2013.01); *C12Q 2600/106* (2013.01); *C12Q 2600/118* (2013.01)

(58) Field of Classification Search
USPC ......... 435/6.1, 6.11, 6.12, 91.1, 91.2, 91.51; 436/94, 501; 536/23.1, 24.3, 24.33
See application file for complete search history.

(56) References Cited

U.S. PATENT DOCUMENTS

| | | | |
|---|---|---|---|
| 5,219,727 A | 6/1993 | Wang et al. | |
| 5,538,871 A | 7/1996 | Nuovo et al. | |
| 5,556,773 A | 9/1996 | Yourno | |
| 5,582,981 A | 12/1996 | Toole et al. | |
| 5,639,606 A | 6/1997 | Willey | |
| 5,639,611 A | 6/1997 | Wallace et al. | |
| 5,840,867 A | 11/1998 | Toole et al. | |
| 6,004,755 A | 12/1999 | Wang | |
| 6,525,154 B1 | 2/2003 | Shea et al. | |
| 6,812,023 B1 | 11/2004 | Lamparski et al. | |
| 6,893,837 B2 | 5/2005 | Slamon et al. | |
| 6,899,863 B1 | 5/2005 | Dhellin et al. | |
| 6,913,879 B1 | 7/2005 | Schena | |
| 6,994,960 B1 | 2/2006 | Foote et al. | |
| 7,074,563 B2 | 7/2006 | Koster | |
| 7,186,512 B2 | 3/2007 | Martienssen et al. | |
| 7,198,893 B1 | 4/2007 | Koster et al. | |
| 7,198,923 B1 | 4/2007 | Abrignani et al. | |
| 7,332,533 B2 | 2/2008 | Kim et al. | |
| 7,364,848 B2 | 4/2008 | Van Beuningen et al. | |
| 7,378,245 B2 | 5/2008 | Liu | |
| 7,384,589 B2 | 6/2008 | Hart et al. | |
| 11,136,627 B2 | 10/2021 | Noerholm et al. | |
| 2010/0196426 A1 | 8/2010 | Skog et al. | |
| 2010/0331240 A1 | 12/2010 | Michelow et al. | |
| 2011/0195426 A1 | 8/2011 | Russo et al. | |
| 2015/0010951 A1 | 1/2015 | LaPointe et al. | |
| 2016/0312211 A1 | 10/2016 | Noerholm | |
| 2021/0403881 A1 | 12/2021 | Stoll et al. | |

FOREIGN PATENT DOCUMENTS

| | | |
|---|---|---|
| CN | 104906117 A | 9/2015 |
| WO | WO-03023065 A1 | 3/2003 |
| WO | WO-03050290 A2 | 6/2003 |
| WO | WO-2006113590 A2 | 10/2006 |
| WO | WO-2009100029 A1 | 8/2009 |
| WO | WO-2011009104 A1 | 1/2011 |
| WO | WO-2012054975 A1 | 5/2012 |
| WO | WO-2014036391 A1 | 3/2014 |

(Continued)

OTHER PUBLICATIONS

Abravaya, et al. 1995. Detection of point mutations with a modified ligase chain reaction (Gap-LCR). Nucleic Acids Res. 23:675-82.
Al-Nedawi, et al., "Intercellular transfer of the oncogenic receptor EGFRvIII by microvesicles derived from tumour cells." Nat Cell Bioi. (2008); 10(5): 619-624.
ATTOSTAR Q-Beta Bacteriophage As An RNA Extraction And RT-PCR Control (online), Attostar LLC, 2007, 9 pages [retrieved on Dec. 14, 2013 from the URL: https://www.attostar.com/ (S(fkpz5czkOzw2ej55q42sd2y3)/PDFs/BAC2000.pdf ].
Balzar, et al., "The biology of the 17-1A antigen (Ep-CAM)." J Mol Med. (1999); 77(10): 699-712.

(Continued)

*Primary Examiner* — Frank W Lu
(74) *Attorney, Agent, or Firm* — COOLEY LLP; Ivor R. Elrifi; Matthew Pavao

(57) ABSTRACT

The present invention features a method and kit for isolating microvesicles or extracting microvesicle nucleic acids from a biological sample by using a control particle. The present invention provides control particles that are viruses or virus-like particles, such as bacteriophages, that contain control nucleic acids that can be detected to assess the accuracy, reliability, and efficiency of the microvesicle isolation or nucleic acid extraction steps. The methods described herein may further comprise the analysis of the presence, absence, or level of at least one biomarker associated with a disease or medical condition for diagnosing, prognosing, or monitoring the disease or medical condition.

10 Claims, 4 Drawing Sheets

Specification includes a Sequence Listing.

(56) References Cited

FOREIGN PATENT DOCUMENTS

| WO | WO-2015021158 A1 | 2/2015 |
| WO | WO-2018076018 A1 | 4/2018 |
| WO | WO-2020106853 A1 | 5/2020 |

OTHER PUBLICATIONS

Bossi et al., "Molecularly imprinted polymers for the recognition of proteins: The state of the art." Biosensors and Bioelectronics (2007); 22(6): 1131-1137.
Cheruvanky, et al., "Rapid isolation of urinary exosomal biomarkers using a nanomembrane ultrafiltration concentrator." Am J Physiol Renal Physiol. (2007); 292: F 1657-F 1661.
Cotton et al., "Reactivity of cytosine and thymine in single-base-pair mismatches with hydroxylamine and osmium tetroxide and its application to the study of mutations", Proc. Natl. Acad. Sci. USA, 85(12):4397-4401 (1988).
Fischer and Lerman, "[11] Two-dimensional electrophoretic separation of restriction enzyme fragments of DNA" Methods in Enzymology (1979); 68: 183-191.
Fischer and Lerman, "Length-independent separation of DNA restriction fragments in two-dimensional gel electrophoresis." Cell (1979); 16(1): 191-200.
Furnari, et al., "Malignant astrocytic glioma: genetics, biology, and paths to treatment." Genes & Dev. (2007); 21: 2683-2710.
Guatelli, et al., "Isothermal, in vitro amplification of nucleic acids by a multienzyme reaction modeled after retroviral replication," Proc Natl Acad Sci U S A. 87(5):1874-1878 (1990).
Hahn, "Molecular biology of double-minute chromosomes." BioEssays (1993); 15(7): 477-484.
Jiang, L., et al., "Synthetic spike-in standards for RNA-seq experiments." Genome Res. (2011); 21(9): 1543-1551. doi: 10.1101/gr.121095.111. Epub Aug. 4, 2011.
Johnson et al., "Surface-immobilized peptide aptamers as probe molecules for protein detection." Anal Chem., 80:978-983 (2008).
Kan and Dozy, "Polymorphism of DNA sequence adjacent to human β-globin structural gene: relationship to sickle mutation." PNAS (1978); 75(11): 5631-5635.
Kan et al., "Antenatal diagnosis of sickle-cell anemia by DNA analysis of amniotic-fluid cells", The Lancet, 312(8096): 910-912 (1978).
Keller, et al., "CD24 is a marker of exosomes secreted into urine and amniotic fluid." Kidney Int. (2007); 72 (9): 1095-1102.
Konoshenko, et al., "Isolation of Extracellular Vesicles: General Methodologies and Latest Trends." BioMed Research International (2018); vol. 2018, Article ID 8545347, 27 pages. https://doi.org/10.1155/2018/8545347.
Kwoh et al., "Transcription-based amplification system and detection of amplified human immunodeficiency virus type 1 with a bead-based sandwich hybridization format (TI RNA polymerase/in vitro nucleic acid amplification) ," Proc. Natl. Acad. Sci. USA, 86:1173-1177 (1989).
Landegren et al., "A ligase-mediated gene detection technique," Science, 241(4869): 1077-1080 (1988), retrieved from http://science.sciencemag.org/ on Oct. 29, 2018.
Li et al., "BEAMing up for detection and quantification of rare sequence variants," Nature Methods, Feb. 2006, vol. 3, No. 2, pp. 95-97.
Li et al., "Replacing PCR with COLD-PCR enriches variant DNA sequences and redefines the sensitivity of genetic testing," Nature Medicine, May 2008, vol. 14, No. 5, pp. 579-584.
Miele et al., "Autocatalytic Replication of a Recombinant RNA," J. Mol. Bioi., 1983, 171, 281-295.
Myers et al., "Detection of Single Base Substitutions by Ribonuclease Cleavage at Mismatches in RNA:DNA Duplexes", Science, 230(4731): 1242-1246 (1985).
Nagrath et al. Isolation of rare circulating tumour cells in cancer patients by microchip technology, Nature 450 (7173): 1235-1239 (Dec. 2007).
Nakazawa, et al., "UV and skin cancer: specific p53 gene mutation in normal skin as a biologically relevant exposure measurement." Proc Natl Acad Sci US A. (1994); 91: 360-364.
Neidler, "What are the differences between PCR, RT-PCR, qPCR, and RT-qPCR?", Posted by Sarah Neidler, Mar. 2017, printed on May 22, 2010, 3 pages.
Pelloski, et al., "Epidermal Growth Factor Receptor Variant III Status Defines Clinically Distinct Subtypes of Glioblastoma." Journal of Clinical Oncology (2007); 25 (16): 2288-2294.
Raposo et al., "B Lymphocytes Secrete Antigen-presenting Vesicles," J Exp Med, Mar. 1996, 183(3): 1161-1172.
Steemers, et al., "Whole-genome genotyping with the single-base extension assay." Nature Methods (2006); 3: 31-33.
Taylor and Gercel-Taylor, "MicroRNA signatures of tumor-derived exosomes as diagnostic biomarkers of ovarian cancer." Gynecol Oncol. (2008); 110: 13-21.
Velculescu et al., "Serial analysis of gene expression," Science 270(5235):484-487 (1995), retrieved from http://science.sciencemag.org/ on Oct. 29, 2018.
Went, P. et al. (2004) Frequent EpCam protein expression in human carcinomas. Human Pathology 35(1):122-128.
Witwer, et al., "Standardization of sample collection, isolation and analysis methods in extracellular vesicle research," J. Extracellular Vesicles, vol. 2: 1-25 (2013).

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 1

```
aacggttctt gtgacccatc                                              20

<210> SEQ ID NO 2
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 2
cgaacaaaag ctcgttcctc                                              20

<210> SEQ ID NO 3
<211> LENGTH: 21
<212> TYPE: DNA
<213> ORGANISM: Artificial Sequence
<220> FEATURE:
<223> OTHER INFORMATION: Chemically synthesized probe

<400> SEQUENCE: 3
cgccaggcat atgctgacgt g                                            21
```

CONTROLS FOR NUCLEIC ACID ASSAYS

RELATED APPLICATIONS

This application is a continuation of U.S. patent application Ser. No. 14/424,694, filed Feb. 27, 2015, now U.S. Pat. No. 11,136,627, issued on Oct. 5, 2021, which is a national stage application, filed under 35 U.S.C. § 371 of International Application No. PCT/US2013/057506, filed Aug. 30, 2013, which claims priority to, and the benefit of, U.S. Provisional Application No. 61/695,116, filed Aug. 30, 2012, the contents of each of which are incorporated herein by reference in their entireties.

INCORPORATION OF SEQUENCE LISTING

The instant application contains a Sequence Listing which has been submitted in ASCII format via EFS-web. The contents of the text filed named "EXOS-008_CO1US_SeqList.txt", which was created on Aug. 23, 2021, and is about 1.06 KB in size, are hereby incorporated by reference in their entirety.

FIELD OF INVENTION

The present invention relates to a kit and methods for isolating a microvesicle fraction and nucleic acids from microvesicles by using a control particle at different steps of the isolation or extraction process.

BACKGROUND

Small membrane-bound vesicles shed by cells are described as "microvesicles". Microvesicles may include exosomes, exosome-like particles, prostasomes, dexosomes, texosomes, ectosomes, oncosomes, apoptotic bodies, retrovirus-like particles, and human endogenous retrovirus (HERV) particles. Studies have shown that microvesicles are shed from many different cell types under both normal and pathological conditions (Thery et al., Nature Reviews Immunology, 2002, 2, pgs. 569-579). Importantly, microvesicles have been shown to contain DNA, RNA, and protein. Recent studies have shown that the analysis of the contents of microvesicles has revealed that biomarkers, or disease-associated genes can be detected, therefore, demonstrating the value of microvesicle analysis for aiding in the diagnosis, prognosis, monitoring, or therapy selection for a disease or other medical disease.

Various molecular diagnostic assays are used to detect disease-related biomarkers and provide valuable information for patients, doctors, clinicians, and researchers. Analysis of nucleic acids extracted from microvesicles for diagnostic purposes has wide-ranging implications due to the non-invasive nature in which microvesicles can be easily collected. Use of microvesicle analysis in place of invasive tissue biopsies would positively impact patient welfare, improve the ability to conduct longitudinal disease monitoring, and improve the ability to obtain expression profiles even when tissue cells are not easily accessible (e.g., in ovarian or brain cancer patients). Thus, the development of additional tools to ensure the consistency, reliability, and practicality of diagnostic microvesicle analysis for use in the clinical field is needed. Without proper internal controls, the results of the nucleic acid analysis could be inconsistent and therefore impractical and for clinical diagnosis. To address this need within the microvesicle diagnostic field, the present invention provides a method and a kit for using a control particle as an internal control for methods of isolating microvesicles and/or extracting nucleic acids from microvesicles.

SUMMARY OF THE INVENTION

The present invention is directed to methods for using control particles as internal controls for isolating microvesicles and/or extracting nucleic acids from microvesicles, and control particles useful for the same. In particular, the methods provided herein are useful for distinguishing high quality extracted nucleic acid samples extracted from the isolated microvesicles that are suitable for further diagnostic or prognostic analysis.

The present invention features a method for isolating microvesicles and/or extracting nucleic acids from the microvesicles from a biological sample by: a) adding a known quantity of control particles that contain control nucleic acids to the biological sample, b) isolating a fraction from the biological sample, c) extracting nucleic acids from the fraction, d) calculating the amount of control particles recovered from the isolation and nucleic acid extraction steps, and e) determining that the amount of control particles recovered (calculated in step (d)) is within a predetermined range of values to distinguish the quality of the microvesicle isolation and/or the nucleic acid extraction. The extracted nucleic acids include nucleic acids from the microvesicles and the control nucleic acids from the control particles. The calculating step may include determining the expression level or copy number of the control nucleic acid of the control particle. In another embodiment, the control particles may be added to the sample after a fraction of microvesicles is isolated and prior to the nucleic acid extraction step.

If the amount of control particles calculated in step (d) is within the predetermined range of values, then the quality of the micovesicle isolation and/or nucleic acid extraction is high. If the amount of control particles calculated in step (d) is not within (i.e., is outside of) the pre-determined range of values, then the quality of the microvesicle isolation and/or nucleic acid extraction is high.

The pre-determined range of values is determined from a collection of reference samples (i.e., a patient cohort). For example, the mean and standard deviation of the levels of expression of the all recovered or detected control nucleic acids (i.e., Ct values) from the collection of reference samples is calculated. The pre-determined range of values may be, for example, 1 standard deviation, 2 standard deviations, 3 standard deviations, 4 standard deviations, or 5 standard deviations from the mean expression level of the recovered control nucleic acids (i.e., Ct values) from the collection of reference samples.

The present invention provides an internal control for methods of isolating microvesicles and extracting nucleic acids from the isolated microvesicles to distinguish the extract nucleic acid samples that are of high quality for accurate and reliable further analysis of disease-associated biomarkers. For example, the extracted nucleic acids are further analyzed for the presence, absence, or change in levels of at least one biomarker associated with a medical condition or disease for diagnosing, prognosing, or monitoring the disease or medical condition. Analysis of the expression level of the control nucleic acid or the presence, absence, or change in levels of at least one biomarker is performed by real-time PCR.

The control particle is a virus particle, such as RNA bacteriophage. Preferably, the control particle is a Q-beta bacteriophage. The control nucleic acid is the gene, or a fragment thereof, that encodes the Q-beta coat protein. The control particle may be naturally-occurring or a recombinant or engineered virus particle.

The biological sample is a bodily fluid. The bodily fluids can be fluids isolated from anywhere in the body of the subject, preferably a peripheral location, including but not limited to, for example, blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid and combinations thereof. For example, the bodily fluid is urine, blood, serum, or cerebrospinal fluid.

In any of the foregoing methods, the nucleic acids are DNA or RNA. Examples of RNA include messenger RNAs, transfer RNAs, ribosomal RNAs, small RNAs (non-protein-coding RNAs, non-messenger RNAs), microRNAs, piR-NAs, exRNAs, snRNAs and snoRNAs.

The present invention provides a kit for isolating a microvesicle fraction and/or microvesicle nucleic acids from a biological sample for the detection of at least one biomarker associated with a disease or medical condition comprising a control particle comprising a known quantity of a control particle comprising a control nucleic acid, primers for hybridization and amplification of the control nucleic acid, and optionally, a set of known concentrations of the control nucleic acid for generating a standard curve, and optionally, instructions for using the foregoing reagents in isolating a microvesicle fraction from a biological sample.

The present invention also provides a kit for determining the quality of a nucleic acid extraction from a microvesicle fraction and/or a nucleic acid extraction comprising a known quantity of a control particle comprising a control nucleic acid, primers for hybridization and amplification of the control nucleic acid, and optionally, a set of known concentrations of the control nucleic acid for generating a standard curve, and optionally, instructions for using the foregoing reagents for determining the quality of the microvesicle extraction and/or nucleic acid extraction from a biological sample.

Various aspects and embodiments of the invention will now be described in detail. It will be appreciated that modification of the details may be made without departing from the scope of the invention. Further, unless otherwise required by context, singular terms shall include pluralities and plural terms shall include the singular.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representations as to the contents of these documents are based on the information available to the applicants and do not constitute any admission as to the correctness of the dates or contents of these documents.

DETAILED DESCRIPTION OF THE INVENTION

Figure 1A:
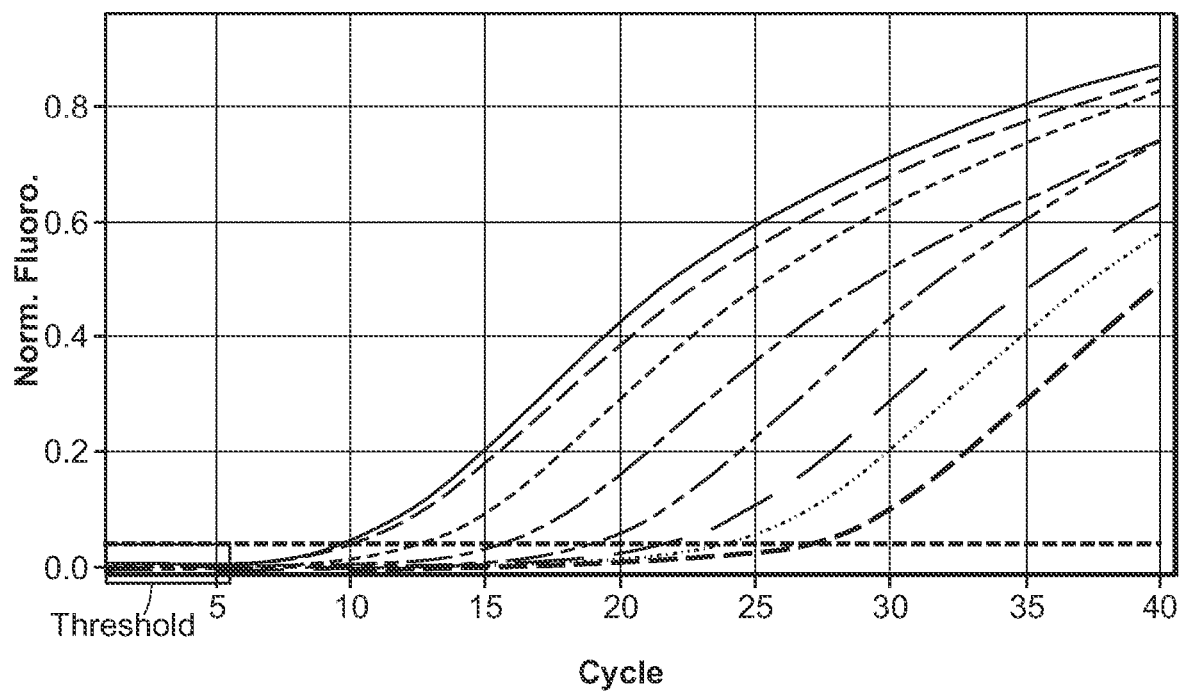
FIG. 1A is a plot of amplification curves in RT-PCR analysis of Q-beta coat protein gene in serum samples. The X axis represents the number of PCR amplification cycles. The Y axis represents the normalized fluorescence, which indicates the magnitude of the signal generated by the given set of PCR conditions.

The present invention is partly based on the discovery that the Q-beta bacteriophage can be utilized as a control particle in methods for isolating microvesicles and extracting microvesicle nucleic acids from a biological sample. Internal controls are often used during isolation and/or extraction processes to determine the efficiency of the process, or the quality of the resulting isolation or extraction. The present method uses control particles, such as Q-beta bacteriophage, that are similar in size to microvesicles to control for the efficiency, quality or purity of the microvesicle isolation and the nucleic acids extracted from the isolated microvesicles.

All membrane vesicles shed by cells <0.8 µm in diameter are referred to herein collectively as microvesicles. This may include exosomes, exosome-like particles, prostasomes, dexosomes, texosomes, ectosomes, oncosomes, apoptotic bodies, retrovirus-like particles, and human endogenous retrovirus (HERV) particles. Microvesicles from various cell sources have been extensively studied with respect to protein and lipid content.

Microvesicles have been previously shown to be valuable diagnostic and prognostic tools. An initial study demonstrated that glioblastoma-derived microvesicles could be isolated from the serum of glioblastoma patients. Importantly, these microvesicles contain mRNA associated with the tumor cells. The nucleic acids within these microvesicles can be used as valuable biomarkers for tumor diagnosis, characterization and prognosis. For example, the nucleic acids within the microvesicles could be used to monitor tumor progression over time by analyzing if other mutations are acquired over time or over the course of treatment. In addition, levels of disease-associated genes can also be determined and compiled into a genetic expression profile which can be compared to reference profiles to diagnose or prognose a disease or monitor the progression of a disease or therapeutic regimen.

The present invention is based on the finding that Q-beta bacteriophage particles can be added to a sample at various steps in microvesicle purification/isolation and microvesicle nucleic acid extraction from a biological sample to serve as an internal control. Thus, the present invention provides methods for addition of a control particle during the extraction of nucleic acids from microvesicles of a biological sample, wherein the control particle serves as an internal control for isolating microvesicles and nucleic acids therefrom. In one aspect, the control particle is added to the biological sample prior to purification of the microvesicles. In another aspect, the control particle is added to the purified microvesicle fraction prior to extraction of the nucleic acids. The quality or purity of the microvesicle fraction or the extracted microvesicle nucleic acids can directly affect the efficiency and sensitivity of the subsequent processes for assaying biomarkers for disease diagnosis, characterization, and prognosis. Given the importance of accurate and sensitive diagnostic tests in the clinical field, the internal control described herein is used to evaluate the quality of the microvesicle purification and microvesicle nucleic acid extraction to increase the reliability and sensitivity of microvesicle-based assays and diagnostics. In particular, the methods and control particles described herein can be used to identify nucleic acid extractions from microvesicles that suitable for further analysis of disease-associated biomarkers for diagnostic, prognostic, and therapeutic applications. Similarly, the methods and control particle described herein can be used to identify nucleic acid extraction that are unsuitable for further analysis of disease-associated biomarkers, or would yield inaccurate results, in diagnostic, prognostic, and therapeutic applications. Thus, the methods described herein can be used to distinguish high quality microvesicle isolations and nucleic acid extractions from low quality microvesicle isolations and nucleic acid extractions, such that the high quality microvesicle isolations or nucleic acid extractions yield accurate results from subsequent analysis steps (i.e., biomarker analysis).

Control Particles

The present invention features the use of control particles as an internal control to isolate microvesicles and/or extract nucleic acids from the isolated microvesicles. In some aspects, the use of the control particles aid in the evaluation of the efficiency and/or quality of microvesicle isolation and/or nucleic acid extraction from the isolated microvesicles.

"Control particles", as used herein, collectively refer to particles of the size range of microvesicles (e.g., less than 0.8 m in diameter) that are added at some point during the microvesicle isolation process (e.g., prior to microvesicle isolation or prior to nucleic acid extraction). The control particles contain control nucleic acids, such as DNA or RNA. Specifically, the control nucleic acids contain target sequences or genes that are assayed or measured to determine the amount of recovered control particles after the isolation or extraction process to distinguish high quality microvesicle isolations or nucleic acid extractions. For example, the control particles are virus particles or virions, such a Q-beta bacteriophage (also referred to herein as Q-beta particles).

In some embodiments, the control particle is a virus particle. Virus particles, as used herein, collectively refers to viruses, virions, and virus-like particles. Virus particles may be naturally-occurring, modified, recombinant, or engineered.

A virus is a small infectious agent that depends on the host cell that it infects to reproduce. Viruses can infect all types of organisms, from animals and plants to bacteria and archaea. Virus particles comprise: a viral genome; a protein coat that protects the genome called the capsid; and a lipid membrane called the viral envelope that surrounds the capsid. Viruses have either DNA or RNA genomes and are called a DNA virus or a RNA virus, respectively. The vast majority of viruses have RNA genomes. The viral genome can be single-stranded or double-stranded, and linear or circular. Viral genome size varies; the smallest is 2 kilobases and encodes only 2 proteins, while the largest viral genome is over 1.2 megabases and encodes over 1,000 proteins. In general, RNA viruses have smaller genome sizes than DNA viruses due to a higher error-rate when replicating. RNA viruses also have a maximum upper size limit. Virus particles can range in size from 0.005 to 0.3 m (or 5-300 nm).

In one embodiment, the control particle is a DNA virus. DNA viruses of the present invention include, but are not limited to, members of the following DNA virus families: Adenoviridae, Papillomaviridae, Parvoviridae, Herpesviridae, Poxviridae, Hepadnaviridae, Polyomaviridae, and Anelloviridae.

In another embodiment, the control particle is a RNA virus. The RNA viruses of the present invention include, but are not limited to, the members of the following RNA virus families: Picornaviridae, Flaviviridae, Filoviridae, Orthomyxoviridae, Paramyxoviridae Togaviridae, Rhabdoviridae, and Retroviridae. For example, the RNA virus is poliovirus, enterovirus, coxsackievirus, echovirus, hepatitis A virus, hepatitis C virus, encephalomyocarditis virus (EMCV), foot-and-mouth disease virus (FMDV), Dengue virus, Yellow Fever Virus, West Nile virus, bovine viral diarrhoea virus (BVDV), eastern encephalitis, western encephalitis, rubella virus, human immunodeficiency virus, simian immunodeficiency virus (SIV), feline immunodeficiency virus, Marburg virus, Ebola virus, influenza virus, measles virus, and rabies virus.

Viruses that can infect bacteria are known as bacteriophages, or phages. There are estimated to be at least several hundred thousands of phage species existing in nature. Phages are classified by morphology (e.g., tailed, polyhedral, filamentous, or pleomorphic) and physiology (e.g., linear or circular genome, single or double stranded genome, or no capsid). Bacteriophages are classified into 11 families: caudovirales, myoviridae, siphoviridae, podoviridae, microviridae, corticoviridae, tectiviridae, leviviridae, cystoviridae, inoviridae, and plasmaviridae. The two classes of RNA bacteriophages are leviviridae and cystoviridae. Leviviridae is characterized by single stranded RNA genomes and cystoviridae is characterized by double-stranded RNA genomes.

In one embodiment, the control particle is a DNA bacteriophage, where the genome is DNA. For example, the bacteriophage is an Ancholeplasma phage, a coliphage, φX174, a spiroplasma phage, or a Mac-1 phage.

In a preferred embodiment, the control particle is a RNA bacteriophage. For example, the control particle is selected from the group consisting of Q-beta, MS2, f2, R17, GA, SP, and φ6.

Preferably, the virus particle is Q-beta bacteriophage. Q-beta is a member of the leviviridae family, and is characterized by a linear, single-stranded RNA genome. The Q-beta bacteriophage genome consists of 3 genes encoding four viral proteins: a coat protein, a maturation protein, a lysis protein, and RNA replicase. Q-beta is about 26 nm in diameter with an icosahedral capsid. Due to its similar size to average microvesicles, Q-beta can be easily purified from a biological sample using the same purification methods described herein for isolating microvesicles. In addition, the low complexity of the Q-beta viral single-stranded gene structure is advantageous for use of Q-beta bacteriophage genes as controls in amplification-based nucleic acid assays.

In other embodiments, the control particle is an engineered or recombinant virus particle, wherein at least one component of the virus particle (e.g., genes or fragments thereof of the genome) is modified, synthesized, or introduced by recombinant DNA or molecular biology techniques known in the art. In other embodiments, the control particle contains a genome that is partially or entirely modified, synthesized, or introduced by recombinant techniques. For example, the recombinant virus particle contains a recombinant RNA genome that includes specific nucleotide sequences corresponding to primers for amplification of a particular sequence of the recombinant RNA genome. The use of the same primer set for amplifying the control nucleic acids and the gene of interest eliminates any risk of interference and/or reduces background signal and false priming by the control virus particle primers. Methods for creating a recombinant virus particle are known in the art. Methods for modifying Q-beta bacteriophage can also be found in Villanova et al. (Villanova et al., 2007).

In other embodiments, the control particle is an engineered microparticle containing control nucleic acids generated by recombinant DNA methods. The control particle is a microvesicle produced by cells in culture.

Use of Control Particles in Microvesicle Analysis

Detection and quantification of control particles recovered after microvesicle isolation and/or nucleic acid extraction is useful for distinguishing high quality microvesicle preparations and/or nucleic acid preparations from low quality microvesicle preparations and/or nucleic acid preparations. As used herein, "microvesicle preparations" refers to the fraction comprising microvesicles after the isolation process. As used herein, "nucleic acid preparations" refers to the extracted nucleic acids from the isolated microvesicles.

In some embodiments, the control particle is of similar size to the size of microvesicles of interest. Control particles can be selected to use as a control based on the size range of the microvesicles to be analyzed, such that the control particle is a similar size to the microvesicle. For example, the control particle is less than 2%, 5%, 10%, 15%, 20% or 50% larger than the microvesicles to be isolated. For example, the control particle is less than 2%, 5%, 10%, 15%, 20% or 50% smaller than the microvesicles to be isolated. Given the size similarity to microvesicles, the control particles can be co-purified with the microvesicles if added to the biological sample prior to the microvesicle purification step.

The control particle of the present invention contains at least one control nucleic acid to be detected. The control nucleic acid can be RNA or DNA. The control nucleic acid can be double-stranded or single stranded. Preferably, the control nucleic acid has low complexity. Low complexity regions are defined as regions composed of only a few elements (i.e., coding regions, non-coding regions, and repeats). Control particles with low complexity control nucleic acids are preferred because the low complexity reduces the potential of false priming with a gene of interest in target microvesicles in the amplification analysis step.

The control nucleic acid of the present invention comprises or is a control target gene or control target sequence to be detected and/or quantified to determine the amount of control particle recovered in a sample after the microvesicle isolation and nucleic extraction process. In one aspect, the control particle is Q-beta bacteriophage and the control target gene is the Q-beta coat protein gene. The control target gene is measured by nucleic acid amplification techniques, using specific primers that recognize the control target gene. In some aspects, a probe is utilized to detect the amplified control target gene. In some aspects, the control nucleic acid or control target gene is measured by RT-PCR analysis.

A known quantity or number of control particles is added to the biological sample prior to microvesicle isolation. The control particles are quantified before being added to the sample. The known quantity or copy number of control particles can be determined by methods known in the art including, but not limited to, tissue culture infective dose, plaque forming units, colony forming units, flow cytometry-based methods, and ELISA assays. The known quantity of control particles or Q-beta particles can be 25, 50, 75, 100, 150, 200, 300, 350, 400, 450, 500, 1,000, or 5,000 copies. Preferably, 50, 100, 200, or 500 copies of Q-beta particles are added to a biological sample. Most preferably, 100 copies of Q-beta particles are added to the biological sample. The copy number of Q-beta particles to be added to the biological sample can be calculated based the ability of the Q-beta particles to infect target cells. Thus, the copy number of Q-beta particles is correlated to the colony forming units of the Q-beta particles utilized.

The control particle may be added to the microvesicle sample to a biological sample, such as urine or serum, prior to isolation of the microvesicle fraction. In this case, the control particle is present during the microvesicle isolation and nucleic acid extraction steps. Because microvesicles and control particles are similar in size, the microvesicle isolation procedure would also successfully isolate the control particles. Therefore, the recovery of the control particles indicates the recovery of microvesicles, and therefore, high recovery of the control particles indicates high quality of the resulting microvesicle preparation.

The control particle may be added to the microvesicle fraction after the microvesicle isolation step, and before the nucleic acid extraction step, thereby creating a mixture comprising the microvesicles isolated from the biological sample and the control particles. Nucleic acids from both the control particle and the microvesicles are extracted in the extraction step. Therefore, the recovery and/or quality of the control nucleic acids from the control particles indicates the recovery and/or quality of nucleic acids from the microvesicles, and therefore, high quality of the control nucleic acids indicates high quality of the resulting nucleic acid preparation comprising microvesicle nucleic acids. In other embodiments, the control particle can be added at other steps during microvesicle analysis.

Calculation of the recovered control particles, as used herein, refers to the quantification or measurement of the control nucleic acid after microvesicle isolation and/or nucleic acid extraction. The level of expression of the control nucleic acid can be measured using any of a variety of art-recognized techniques, including, but not limited to, real-time quantitative PCR. For example, RT-PCR analysis determines a Ct (cycle threshold) value for each reaction. In RT-PCR, a positive reaction is detected by accumulation of a fluorescence signal. The Ct value is defined as the number of cycles required for the fluorescent signal to cross the threshold (i.e., exceeds background level). Ct levels are inversely proportional to the amount of target nucleic acid, or control nucleic acid, in the sample (i.e., the lower the Ct level, the greater the amount of control nucleic acid in the sample).

In another embodiment, the copy number of the control nucleic acid can be measured using any of a variety of art-recognized techniques, including, but not limited to, RT-PCR. Copy number of the control nucleic acid can be determined using methods known in the art, such as by generating and utilizing a calibration, or standard curve.

A standard curve can be generated using known concentrations and copy numbers of a standard nucleic acid in the subsequent quantification analysis (e.g., RT-PCR). The standard nucleic acid is similar or identical to the control nucleic acid of the control particle (e.g., has a similar or identical sequence). The standard target gene is quantified using the same methods to quantify the control target gene, as disclosed herein.

For example, a standard curve is generated using 10-fold dilutions of the standard nucleic acid. In some aspects, the standard curve is generated by using at least 2, 3, or 4 known concentrations/copy numbers of standard nucleic acids. The dilution samples of the standard nucleic acid is quantified by methods used herein, e.g., RT-PCR or quantitative PCR analysis. Preferably, the dilution series is analyzed on the same plate as the samples being analyzed for the quality of the microvesicle isolation and/or nucleic acid extraction methods. The calculated Ct or copy number from the RT-PCR analysis of each dilution, with respect to the known concentration, is used to generate a standard curve. Extrapolation of the standard curve can be used to calculate the copy numbers of control particles after quantification of the control particles. By comparing the Ct values of the samples being analyzed for the quality of the isolation and/or extraction to the Ct values of the calibration curves, the exact copy number of the control particles recovered in the analyzed samples can be determined.

Copy numbers are calculated by fitting a curve of the following formula $$Ct = b + a * \log 10(\text{Calibration\_Copies})$$

To the known calibration points on the dilution series on the plate to achieve the "calibration curve". Copy numbers for samples are then calculated by the formula $$\text{Sample\_Copies} = 10^{((Ct\_Sample - b)/a)}$$

This copy number calculation is done independently for each sample.

The calculated copy number or level of expression (i.e., Ct value) of the control nucleic acid is the amount or quantity of control particles or Q-beta particles recovered from the microvesicle isolation and/or nucleic acid extraction processes.

The quality of a microvesicle isolation and/or nucleic acid extraction is then determined by comparing the amount, or calculated copy number of the recovered control particles (or control nucleic acids) to a pre-determined cutoff value. If the calculated amount of control particles is higher than the pre-determined cutoff value, then the quality of the micovesicle isolation and/or nucleic acid extraction is high. If the calculated amount of control particles is lower than the pre-determined cutoff value, then the quality of the microvesicle isolation and/or nucleic acid extraction is low. In another aspect, if the calculated amount of control particles is within 1%, 2%, 3%, 4%, 5%, 6%, 7%, 8%, 9%, 10%, 15%, 20%, 25%, 30%, 35%, 40%, 45% or 50% of the known quantity of the control particles first added to the biological sample prior to microvesicle isolation or nucleic acid extraction, then the quality of the isolation and/or extraction is high.

In some embodiments, the predetermined cutoff threshold is a measured value from the quantification analysis, e.g., for RT-PCR analysis, the pre-determined cutoff value is a Ct value. For example, the quality of the microvesicle isolation or nucleic acid extraction is high if the Ct value is below 25, below 26, below 27, below 28, below 29, or below 30. The quality of the microvesicle isolation or nucleic acid extraction is low if the Ct value is above 27, above 28, above 29, or 30.

In one aspect, the pre-determined range of values indicates that the biological sample has been successfully processed. In one aspect, the pre-determined range of values indicates that the microvesicle fraction has been successfully isolated. In one aspect, the pre-determined range of values indicates that the nucleic acids have been successfully processed. The pre-determined range of values is within 50%, 55%, 60%, 65%, 70%, 75%, 80%, 85%, 90%, or 95% of the number of control particles added to the sample prior to the microvesicle isolation or nucleic acid extraction steps. Preferably, the pre-determined range of values is greater than 80% of the number of control particles added to the sample. Preferably, the pre-determined range of values is greater than 85% of the number of control particles added to the sample. More preferably, the pre-determined range of values is greater than 90% of the number of control particles added to the sample. Most preferably, the pre-determined range of values is greater than 95% of the number of control particles added to the sample. In some embodiments, the pre-determined range of values is indicated by the measured value from the quantification analysis, e.g., for RT-PCR analysis, the pre-determined range of values is a Ct value, between 25-30, 20-30, 15-30, or 10-30.

In other embodiments, the amount of control particles recovered (i.e., expression level detected of the control nucleic acid, or Ct value) is compared to a predetermined range of values. The predetermined range of values is determined from a collection of reference samples (i.e., a patient cohort). The collection of reference samples have been processed using the microvesicle and nucleic acid extraction methods disclosed herein. A control particle is added to the sample prior to microvesicle isolation or prior to nucleic acid extraction. The mean of the levels of expression of the recovered or detected control nucleic acids (i.e., Ct values) from the collection of reference samples is calculated. The standard deviation from the mean of all the recovered or detected control nucleic acids from the collection of reference samples is also calculated. The pre-determined range of values may be, for example, 1 standard deviation, 2 standard deviations, 3 standard deviations, 4 standard deviations, or 5 standard deviations from the mean expression level of the recovered control nucleic acids (i.e., Ct values) from the collection of reference samples. Preferably, the pre-determined range of values is 3 standard deviations from the mean Ct value of the recovered control nucleic acids from the reference samples. For example, if the Ct value of the recovered control nucleic acid from a biological sample is within 3 standard deviations of the mean Ct value of the recovered control nucleic acid of the collection of reference samples, then the extracted nucleic acids (or nucleic acid preparation) is of high quality and would be sufficient for further biomarker analysis. If the Ct value of the recovered control nucleic acid from a biological sample is not within 3 standard deviations, or is outside 3 standard deviations, of the mean Ct value of the recovered control nucleic acid of the collection of reference samples, then the extracted nucleic acids (or nucleic acid preparation) is of low quality and would not be sufficient for further biomarker analysis. Low quality nucleic acid preparations would not yield accurate or reliable results in biomarker analysis for diagnosis, prognosis, or therapy selection for a patient.

Samples in which no control nucleic acids are detected (i.e., no qPCR or RT-PCR signal) are also deemed low quality and not suitable for further biomarker analysis.

The collection of reference samples may include healthy individuals that have not been diagnosed with a disease, for example, cancer. The collection of reference samples may include individuals that have been diagnosed with a disease, for example, cancer, or have a positive biopsy status. The cancer can be any kind of cancer or pre-cancerous condition. This includes, without limitation, epithelial cell cancers such as lung, ovarian, cervical, endometrial, breast, brain, colon and prostate cancers. Also included are gastrointestinal cancer, head and neck cancer, non-small cell lung cancer, cancer of the nervous system, retina cancer, skin cancer, liver cancer, pancreatic cancer, genital cancer and bladder cancer, melanoma, and leukemia.

The methods disclosed in the present invention can be used to determine whether the microvesicle preparations and/or nucleic acid preparations are of sufficient quality for further analysis of at least one disease-associated biomarker for diagnostic, prognostic, and therapeutic applications. For example, if the quality of the microvesicle isolation or nucleic acid extraction is determined to be high using the methods disclosed herein, then the extracted nucleic acids (or nucleic acid preparation) can be used for further analysis to aid in the diagnosis, prognosis or therapy selection for a disease or a medical condition. Conversely, if the quality of the microvesicle isolation or nucleic acid extraction is determined to be low using the methods disclosed herein, then the extracted nucleic acids should not be used for further analysis, as the low quality or efficiency from the isolation and/or extraction methods indicates that any further analysis may be inaccurate.

The present invention also provides methods for using multiple control particles for determining the quality or efficiency of multiple steps independently, such as microvesicle isolation and nucleic acid extraction, of the same sample. In this manner, for example, the quality of the microvesicle purification and the nucleic acid extraction can be evaluated in a single sample for a single analysis. For example, a Q-beta bacteriophage control particle can be added prior to the microvesicle isolation step and a MS2 bacteriophage control particle can be added prior to the RNA extraction step. After reverse-transcription of extracted RNA (which will contain RNA from the microvesicles, Q-beta bacteriophage, and MS2 bacteriophage), the RNA levels can be quantified using real-time PCR and Q-beta and MS2-specific probes. The use of multiple, distinct control particles will allow simultaneous analysis of the quality of microvesicle purification and RNA extraction for each sample.

Microvesicles as Diagnostic and Prognostic Tools

The present invention is based on the finding that addition of Q-beta particles to a sample at various steps during microvesicle analysis serves as a control for high quality microvesicle isolations and/or nucleic acid extractions with high recovery and yield of the resulting extracted nucleic acids. The quality, or purity of the microvesicles can directly affect the efficiency and sensitivity of the subsequent processes for assaying biomarkers for diagnosis, characterization, and prognosis of a disease or medical condition.

For example, biological samples are first processed to remove cells and other large contaminants. This first pre-processing step can be accomplished by using a 0.8 m filter to separate cells and other cell debris from the microvesicles. Optionally, centrifugation (i.e., slow centrifugation) can be used to further separate contaminants from the microvesicles. Control particles are added to the pre-processed sample at a known quantity. Additional processing is performed to isolate a fraction containing microvesicles and control particles. Suitable additional processing steps include filtration concentrators and differential centrifugation. The fraction containing microvesicles and control particles is washed to remove additional contaminants at least once. The fraction may be washed once, twice, three times, four times, or five times using a physiological buffer, such as phosphate-buffered saline. RNase inhibitor was added to the fraction, preferably to the fraction located in the upper chamber of the filter concentrator. Lysis of the microvesicles and control particles can be optionally performed in the upper chamber of the filter concentrator.

The method of isolating microvesicles from a biological sample and extracting nucleic acids from the isolated microvesicles may be achieved by many methods. Some of these methods are described in publications WO 2009/100029 and WO 2011/009104, both of which are hereby incorporated in their entirety. In one embodiment, the method comprises the following steps: removing cells from the bodily either by low speed centrifugation and/or filtration though a 0.8 μm filter; centrifuging the supernatant/filtrate at about 120,000 xg for about 0.5 hour at about 4° C.; treating the pellet with a pre-lysis solution, e.g., an RNase inhibitor and/or a pH buffered solution and/or a protease enzyme in sufficient quantities; and lysing the pellet for nucleic acid extraction. The lysis of microvesicles in the pellet and extraction of nucleic acids may be achieved with various methods known in the art (e.g., using commercially available kids (e.g., Qiagen) or phenol-chloroform extraction according to standard procedures and techniques known in the art). Control particles can be added, at least, prior to the microvesicle isolation step or prior to the RNA extraction step.

Additional methods of isolating microvesicles from a biological sample are known in the art. For example, a method of differential centrifugation is described by Raposo et al. (Raposo et al., *Journal of Experimental Medicine*, 1996, 183(3), pgs. 1161-1172). Methods of anion exchange and/or gel permeation chromatography are described in U.S. Pat. Nos. 6,899,863 and 6,812,023. Methods of sucrose density gradients or organelle electrophoresis are described in U.S. Pat. No. 7,198,923. A method of magnetic activated cell sorting (MACS, Miltenyi) is described in (Taylor and Gercel-Taylor, *Gynecologic Oncology*, 2008, 110, pgs. 13-21). A method of nanomembrane ultrafiltration concentrator is described in (Cheruvanky et al., *Am J Physiol Renal*

*Physiol,* 2007, 292(5), pgs. F1657-1661). Preferably, microvesicles can be identified and isolated from bodily fluid of a subject by a newly developed microchip technology that uses a unique microfluidic platform to efficiently and selectively separate tumor derived microvesicles. This technology, as described in a paper by Nagrath et al. (Nagrath et al., *Nature,* 2007, 450(7173), pgs. 1235-1239), can be adapted to identify and separate microvesicles using similar principles of capture and separation as taught in the paper. Each of the foregoing references is incorporated by reference herein for its teaching of these methods.

In one embodiment, the microvesicles isolated from a bodily fluid are enriched for those originating from a specific cell type, for example, lung, pancreas, stomach, intestine, bladder, kidney, ovary, testis, skin, colorectal, breast, prostate, brain, esophagus, liver, placenta, fetus cells. Because the microvesicles often carry surface molecules such as antigens from their donor cells, surface molecules may be used to identify, isolate and/or enrich for microvesicles from a specific donor cell type (Al-Nedawi et al., *Nature Cell Biology,* 2008, 10(5), pgs. 619-624; Taylor and Gercel-Taylor, *Gynecologic Oncology,* 2008, 110, pgs. 13-21). In this way, microvesicles originating from distinct cell populations can be analyzed for their RNA content. For example, tumor (malignant and nonmalignant) microvesicles carry tumor-associated surface antigens and may be detected, isolated and/or enriched via these specific tumor-associated surface antigens. In one example, the surface antigen is epithelial-cell-adhesion-molecule (EpCAM), which is specific to microvesicles from carcinomas of lung, colorectal, breast, prostate, head and neck, and hepatic origin, but not of hematological cell origin (Balzar et al., *J Mol Med* (Berl.), 1999, 77(10), pgs. 699-712; Went et al., *Human Pathology,* 2004, 35(1), pgs. 122-128). In another example, the surface antigen is CD24, which is a glycoprotein specific to urine microvesicles (Keller et al., *Kidney International,* 2007, 72(9), pgs. 1095-1102). In yet another example, the surface antigen is selected from a group of molecules CD70, carcinoembryonic antigen (CEA), EGFR, EGFRvIII and other variants, Fas ligand, TRAIL, tranferrin receptor, p38.5, p97 and HSP72. Additionally, tumor specific microvesicles may be characterized by the lack of surface markers, such as CD80 and CD86.

The isolation of microvesicles from specific cell types can be accomplished, for example, by using antibodies, aptamers, aptamer analogs or molecularly imprinted polymers specific for a desired surface antigen. In one embodiment, the surface antigen is specific for a cancer type. In another embodiment, the surface antigen is specific for a cell type which is not necessarily cancerous. One example of a method of microvesicle separation based on cell surface antigen is provided in U.S. Pat. No. 7,198,923. As described in, e.g., U.S. Pat. Nos. 5,840,867 and 5,582,981, WO2003/050290 and a publication by Johnson et al. (Johnson et al., *Anal Chem,* 2008, 80(4), pgs. 978-983), aptamers and their analogs specifically bind surface molecules and can be used as a separation tool for retrieving cell type-specific microvesicles. Molecularly imprinted polymers also specifically recognize surface molecules as described in, e.g., U.S. Pat. Nos. 6,525,154, 7,332,553 and 7,384,589 and a publication by Bossi et al. (Bossi et al., *Biosens Bioelectron,* 2007, 22(6), pgs. 1131-1137) and are a tool for retrieving and isolating cell type-specific microvesicles. Each of the foregoing reference is incorporated herein for its teaching of these methods.

In some embodiments, it may be beneficial or otherwise desirable to amplify the nucleic acid of the microvesicle prior to analyzing it. Methods of nucleic acid amplification are commonly used and generally known in the art, many examples of which are described herein. If desired, the amplification can be performed such that it is quantitative. Quantitative amplification will allow quantitative determination of relative amounts of the various nucleic acids, to generate a genetic or expression profile.

In one embodiment, the nucleic acid extracted from the microvesicles is DNA. In one embodiment, the nucleic acid extracted from the microvesicles is RNA. RNA may include messenger RNAs, transfer RNAs, ribosomal RNAs, small RNAs (non-protein-coding RNAs, non-messenger RNAs), microRNAs, piRNAs, exRNAs, snRNAs and snoRNAs.

In some aspects, the RNA is preferably reverse-transcribed into complementary DNA (cDNA) before further amplification. RNAs are then preferably reverse-transcribed into complementary DNAs before further amplification. Such reverse transcription may be performed alone or in combination with an amplification step. One example of a method combining reverse transcription and amplification steps is reverse transcription polymerase chain reaction (RT-PCR), which may be further modified to be quantitative, e.g., quantitative RT-PCR as described in U.S. Pat. No. 5,639,606, which is incorporated herein by reference for this teaching. The extracted nucleic acids or complementary DNA can be analyzed for diagnostic purposes by nucleic acid amplification.

Nucleic acid amplification methods include, without limitation, polymerase chain reaction (PCR) (U.S. Pat. No. 5,219,727) and its variants such as in situ polymerase chain reaction (U.S. Pat. No. 5,538,871), quantitative polymerase chain reaction (U.S. Pat. No. 5,219,727), nested polymerase chain reaction (U.S. Pat. No. 5,556,773), self-sustained sequence replication and its variants (Guatelli et al., *Proc Nat Acad Sci USA,* 1990, 87(5), pgs. 1874-1878), transcriptional amplification system and its variants (Kwoh et al., *Proc Natd Acad Sci USA,* 1989, 86(4), pgs 1173-1177), Qb Replicase and its variants (Miele et al., *J Mol Biol,* 1983, 171(3), pgs. 281-295), cold-PCR (Li et al., *Nature Medicine,* 2008, 14(5), pgs. 579-584), BEAMing (Li et al., *Nature Methods,* 2006, 3(2), pgs. 95-97) or any other nucleic acid amplification methods, followed by the detection of the amplified molecules using techniques well known to those of skill in the art. Especially useful are those detection schemes designed for the detection of nucleic acid molecules if such molecules are present in very low numbers. The foregoing references are incorporated herein for their teachings of these methods. In other embodiment, the step of nucleic acid amplification is not performed. Instead, the extract nucleic acids are analyzed directly (e.g., through next-generation sequencing).

The analysis of nucleic acids present in the isolated particles is quantitative and/or qualitative. For quantitative analysis, the amounts or expression levels, either relative or absolute, of specific nucleic acids of interest within the isolated particles are measured with methods known in the art. For qualitative analysis, the species of specific nucleic acids of interest within the isolated particles, whether wild type or variants, are identified with methods known in the art.

The present invention also includes methods for microvesicle nucleic acid analysis with the presence of control particles for (i) aiding in the diagnosis of a subject, (ii) monitoring the progress or reoccurrence of a disease or other medical condition in a subject, or (iii) aiding in the evaluation of treatment efficacy for a subject undergoing or contemplating treatment for a disease or other medical condition; wherein the presence or absence of one or more biomarkers in the nucleic acid extraction obtained from the method is determined, and the one or more biomarkers are associated with the diagnosis, progress or reoccurrence, or treatment efficacy, respectively, of a disease or other medical condition.

The one or more biomarkers can be one or a collection of genetic aberrations, which is used herein to refer to the nucleic acid amounts as well as nucleic acid variants within the nucleic acid-containing particles. Specifically, genetic aberrations include, without limitation, over-expression of a gene (e.g., an oncogene) or a panel of genes, under-expression of a gene (e.g., a tumor suppressor gene such as p53 or RB) or a panel of genes, alternative production of splice variants of a gene or a panel of genes, gene copy number variants (CNV) (e.g., DNA double minutes) (Hahn, 1993), nucleic acid modifications (e.g., methylation, acetylation and phosphorylations), single nucleotide polymorphisms (SNPs), chromosomal rearrangements (e.g., inversions, deletions and duplications), and mutations (insertions, deletions, duplications, missense, nonsense, synonymous or any other nucleotide changes) of a gene or a panel of genes, which mutations, in many cases, ultimately affect the activity and function of the gene products, lead to alternative transcriptional splice variants and/or changes of gene expression level, or combinations of any of the foregoing.

The determination of such genetic aberrations can be performed by a variety of techniques known to the skilled practitioner. For example, expression levels of nucleic acids, alternative splicing variants, chromosome rearrangement and gene copy numbers can be determined by microarray analysis (see, e.g., U.S. Pat. Nos. 6,913,879, 7,364,848, 7,378,245, 6,893,837 and 6,004,755) and quantitative PCR. Particularly, copy number changes may be detected with the Illumina Infinium II whole genome genotyping assay or Agilent Human Genome CGH Microarray (Steemers et al., 2006). Nucleic acid modifications can be assayed by methods described in, e.g., U.S. Pat. No. 7,186,512 and patent publication WO2003/023065. Particularly, methylation profiles may be determined by Illumina DNA Methylation OMA003 Cancer Panel. SNPs and mutations can be detected by hybridization with allele-specific probes, enzymatic mutation detection, chemical cleavage of mismatched heteroduplex (Cotton et al., *Proc Natl Acad Sci USA* 1988, 85(12), pgs 4397-4401), ribonuclease cleavage of mismatched bases (Myers et al., *Science,* 1985, 230(4731), pgs. 1242-1246), mass spectrometry (U.S. Pat. Nos. 6,994,960, 7,074,563, and 7,198,893), nucleic acid sequencing, single strand conformation polymorphism (SSCP) (Orita et al., 1989), denaturing gradient gel electrophoresis (DGGE)(Fischer and Lerman, *Methods Enzymology,* 1979, 68, pgs. 183-191; Fischer and Lerman, *Cell,* 1979, 16(1), pgs. 191-200), temperature gradient gel electrophoresis (TGGE) (Fischer and Lerman, 1979a; Fischer and Lerman, 1979b), restriction fragment length polymorphisms (RFLP) (Kan and Dozy, *Lancet,* 1978, 2(8096), pgs. 910-912; Kan and Dozy, *Proce Natl Acad Sci USA,* 1978, 75(11), pgs. 5631-5635), oligonucleotide ligation assay (OLA), allele-specific PCR (ASPCR) (U.S. Pat. No. 5,639,611), ligation chain reaction (LCR) and its variants (Abravaya et al., *Nucleic Acids Research,* 1995, 23(4), pgs. 675-682; Landegren et al., *Science,* 1988, 241(4869), pgs. 1077-1080; Nakazawa et al., *Proc Natl Acad Sci USA,* 1994, 91(1), pgs. 360-364), flow-cytometric heteroduplex analysis (WO/2006/113590) and combinations/modifications thereof. Notably, gene expression levels may be determined by the serial analysis of gene expression (SAGE) technique (Velculescu et al., *Science,* 1995, 5235, pgs. 484-487). In general, the methods for analyzing genetic aberrations are reported in numerous publications, not limited to those cited herein, and are available to skilled practitioners. The appropriate method of analysis will depend upon the specific goals of the analysis, the condition/history of the patient, and the specific cancer (s), diseases or other medical conditions to be detected, monitored or treated. The forgoing references are incorporated herein for their teaching of these methods.

Many biomarkers may be associated with the presence or absence of a disease or other medical condition in a subject. Therefore, detection of the presence or absence of such biomarkers in a nucleic acid extraction from isolated particles, according to the methods disclosed herein, may aid diagnosis of the disease or other medical condition in the subject. For example, as described in WO 2009/100029, detection of the presence or absence of the EGFRvIII mutation in nucleic acids extracted from microvesicles isolated from a patient serum sample may aid in the diagnosis and/or monitoring of glioblastoma in the patient. This is so because the expression of the EGFRvIII mutation is specific to some tumors and defines a clinically distinct subtype of glioma (Pelloski et al., *J Clin Oncol* 2007, 25(16), pgs. 2288-2294). For another example, as described in WO 2009/100029, detection of the presence or absence of the TMPRSS2-ERG fusion gene and/or PCA-3 in nucleic acids extracted from microvesicles isolated from a patient urine sample may aid in the diagnosis of prostate cancer in the patient. For another example, detection of presence or absence of the combination of ERG and AMACR in a bodily fluid may aid in the diagnosis of cancer in a patient.

Further, many biomarkers may help disease or medical status monitoring in a subject. Therefore, the detection of the presence or absence of such biomarkers in a nucleic acid extraction from isolated particles, according to the methods disclosed herein, may aid in monitoring the progress or reoccurrence of a disease or other medical condition in a subject. For example, as described in WO 2009/100029, the determination of matrix metalloproteinase (MMP) levels in nucleic acids extracted from microvesicles isolated from an organ transplantation patient may help to monitor the post-transplantation condition, as a significant increase in the expression level of MMP-2 after kidney transplantation may indicate the onset and/or deterioration of post-transplantation complications. Similarly, a significantly elevated level of MMP-9 after lung transplantation, suggests the onset and/or deterioration of bronchiolitis obliterans syndrome.

Many biomarkers have also been found to influence the effectiveness of treatment in a particular patient. Therefore, the detection of the presence or absence of such biomarkers in a nucleic acid extraction from isolated particles, according to the methods disclosed herein, may aid in evaluating the efficacy of a given treatment in a given patient. For example, as disclosed in Table 1 in the publication by Furnari et. al. (Furnari et al., *Genes Development,* 2007, 21(21), pgs. 2683-2710), biomarkers, e.g., mutations in a variety of genes, affect the effectiveness of specific medicines used in chemotherapy for treating brain tumors. The identification of these biomarkers in nucleic acids extracted from isolated particles from a biological sample from a patient may guide the selection of treatment for the patient.

In certain embodiments of the foregoing aspects of the invention, the disease or other medical condition is a neoplastic disease or condition (e.g., cancer or cell proliferative disorder), a metabolic disease or condition (e.g., diabetes, inflammation, perinatal conditions or a disease or condition associated with iron metabolism), a neurological disease or condition, an immune disorder or condition, a post transplantation condition, a fetal condition, or a pathogenic infection or disease or condition associated with an infection.

As used herein, the term "biological sample" refers to a sample that contains biological materials such as a DNA, a RNA and/or a protein. In some embodiments, the biological sample may suitably comprise a bodily fluid from a subject. The bodily fluids can be fluids isolated from anywhere in the body of the subject, preferably a peripheral location, including but not limited to, for example, blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid and combinations thereof. In some embodiments, the preferred body fluid for use as the biological sample is urine. In other embodiments, the preferred body fluid is serum. In still other embodiments, the preferred body fluid is cerebrospinal fluid.

Suitably a biological sample volume of about 0.1 ml to about 30 ml fluid may be used. The volume of fluid may depend on a few factors, e.g., the type of fluid used. For example, the volume of serum samples may be about 0.1 ml to about 2 ml, preferably about 1 ml. The volume of urine samples may be about 10 ml to about 30 ml, preferably about 20 ml.

The term "subject" is intended to include all animals shown to or expected to have nucleic acid-containing particles. In particular embodiments, the subject is a mammal, a human or nonhuman primate, a dog, a cat, a horse, a cow, other farm animals, or a rodent (e.g. mice, rats, guinea pig. etc.). A human subject may be a normal human being without observable abnormalities, e.g., a disease. A human subject may be a human being with observable abnormalities, e.g., a disease. The observable abnormalities may be observed by the human being himself, or by a medical professional. The term "subject", "patient", and "individual" are used interchangeably herein.

Kit for Use of Viral Control Particles:

The present invention also features a kit for isolating microvesicles and microvesicle-derived nucleic acids from a biological sample and distinguishing the quality of a microvesicle isolation or nucleic acid extraction for the subsequent analysis or detection of at least one biomarker associated with a disease or medical condition. The kit is comprises the following components: a known quantity of a control particle comprising a control nucleic acid, control nucleic acid-specific primers, and optionally a control nucleic acid-specific probe, optionally, a set of known concentration dilutions of the control nucleic acid for generating a standard curve, and optionally, instructions for using the foregoing reagents for isolating a microvesicle fraction from a biological sample.

Optionally, the kit may also include a lysis buffer, a filtration concentrator, a DNase or RNase inhibitor, to increase the quality or purity of nucleic acid extraction. The control particle aids in assessing the accuracy, reliability, and efficiency of each step in the isolation or purification process. The lysis buffer breaks open microvesicles to release their nucleic acid contents. The use of RNAse inhibitors and DNase enhances the quality of the extracted nucleic acids. The filtration concentrator is used to isolate and concentrate particles from a biological sample. Other methods known in the art, such as centrifugation may also be used to isolate particles from a biological sample. The filtration concentrator and centrifugation steps can also be performed sequentially for isolation of microvesicles and control particles. The kit may also comprise instructions that detail the steps as appropriate for using the kit components in connection with the extraction of nucleic acids from isolated particles.

It should be understood that this invention is not limited to the particular methodologies, protocols and reagents, described herein, which may vary. The terminology used herein is for the purpose of describing particular embodiments only, and is not intended to limit the scope of the present invention, which is defined solely by the claims.

Examples of the disclosed subject matter are set forth below. Other features, objects, and advantages of the disclosed subject matter will be apparent from the detailed description, figures, examples and claims. Methods and materials substantially similar or equivalent to those described herein can be used in the practice or testing of the presently disclosed subject matter.

EXAMPLES

Example 1: Q-Beta Bacteriophage as an Internal Control for Serum RNA Analysis

In this example, Q-beta bacteriophage was utilized as an internal control for microvesicle and RNA extraction from human serum samples. A serum sample was obtained from a normal, healthy human volunteer, and aliquoted into four 1 mL samples (labeled A, B, C, and D). Each aliquot was filtered through a 0.8 µm filter (Millipore) and the filtrate was then stored at −80° C. for 24 hours. After the samples were thawed, 8 µl of SuperaseIn RNase inhibitor was added to each sample and incubated for 5 minutes. 5 µl of Q-beta bacteriophage (Attostar Catalog No. BAC200) was added to samples A and C. Next, 2.5 ml PBS was added to all four samples and spun at 120,000×g for 60 minutes at 4° C. to obtain microvesicle particle pellets. The particles were washed in PBS and pelleted by centrifugation. At this point, 5 µl Q-beta bacteriophage was added to samples B and D. All four samples were then treated with a mixture of RNA inhibitors and DNase at room temperature for 20 minutes.

The mixture of DNase and SuperaseIn RNase inhibitor was prepared as follows and added to each sample:

| | |
|---|---|
| DNase 1 | 2 µL |
| DNase buffer (10X) | 5 µL |
| SuperaseIn | 8 µL |
| 1xPBS | 35 µL |
| | 50 µL |

The DNase 1 and DNase buffer is from TURBO DNA-free™ kit from Ambion. SuperaseIn was used at a concentration of 20 units/µL.

RNA was extracted from the microvesicle and particle mixture by chloroform extraction. Microvesicles were lysed with 700 µl Qiazol lysis buffer, and the RNA was extracted with 140 µl chloroform in each sample. After chloroform extraction, the aqueous was transferred to a new collection tube and 1.5× volumes of 100% ethanol was added to precipitate the RNA. Once precipitated, the RNA was washed in a RNeasy Micro spin column (Qiagen) once with 700 µl RWT buffer and then twice with 500 µl RPE buffer (Qiagen). The RNA on the column was eluted in 16 µl nuclease-free H$_2$O.

The Q-beta coat protein gene was used as the control target gene in this example. Quantification of the Q-beta coat protein gene expression was analyzed by real-time PCR (RT-PCR). Briefly, 12 µl from each of the extracted RNA samples were reverse-transcribed into cDNA using a VILO™ kit (Invitrogen). The reverse transcription reaction mixture was prepared according to the following scheme (Table 1).

TABLE 1

Reverse transcription reaction mixture scheme.

|  | (µl) × 1 reaction | ×4.4 |
|---|---|---|
| 5X VILO ™ Reaction Mix | 4 | 17.6 |
| 10X SuperScript ® Enzyme Mix | 2 | 8.8 |
| RNA (up to 2.5 µg) | 12 | — |
| Nuclease free water | 2 | 8.8 |
| Total volume | 20 |  |

The reverse transcription was performed in a Veriti Thermal Cycler (Applied Biosystems) under the following conditions: 25° C. for 10 minutes, 42° C. for 70 minutes, 85° C. for 5 minutes, and was held in 4° C. before the reaction was stored at −20° C.

The amount of Q-beta coat protein RNA in each sample was quantified by real-time PCR. The primers-probe for the Q-beta coat protein gene was from Attostar catalog No. PP250. The Q-beta coat protein gene forward primer is as follows: 5'-AACGGTTCTTGTGACCCATC-3' (SEQ ID NO: 1). The Q-beta coat protein gene reverse primer is as follows: 5'-CGAACAAAAGCTCGTTCCTC-3' (SEQ ID NO: 2). The Q-beta coat protein gene probe is as follows: 5'-CGCCAGGCATATGCTGACGTG-3' (SEQ ID NO: 3). The real-time PCR master mix was LightCycler® FastStart DNA Master HybProbe (Roche). The real-time PCR mixture was prepared according to the scheme in Table 2. Each real-time PCR sample contained 5 µl of prepared cDNA, for a total reaction volume of 20 µl. The real-time PCR was performed under the following conditions: 95° C. for 10 minutes; 40 cycles of 95° C. for 10 seconds, 55° C. for 15 seconds, and 72° C. for 20 seconds.

TABLE 2

Reverse transcription reaction mixture scheme.

| Component | Volume (µl)/reaction |
|---|---|
| H2O | 7.8 |
| 25 mM MgCl2 | 3.2 |
| 10X QB Primers-probe Quasar670-BHQ2 | 2 |
| 10X LightCycler ® FastStart DNA Master HybProbe | 2 |
| cDNA sample | 5 |
| Final reaction Volume | 20 |

For the purposes of standardization, Q-beta plasmid DNA (Attostar catalog No. PLAS200), containing the Q-beta coat protein gene, were used as templates in the real-time PCR. The Q-beta plasmid DNA was diluted in water sequentially at 10 fold to generate Q-beta plasmid concentrations of: 200 pg/ml, 20 pg/ml, 2 pg/ml, 0.2 pg/ml, and 0.02 pg/ml. The 0.02 pg/ml plasmid solution contains 12 copies of Q-beta plasmid in 1 µl. 5 µl diluted Q-beta plasmid at 20 pg/ml (60,000 copies/rxn), 2 pg/ml (6,000 copies/rxn), 0.2 pg/ml (600 copies/rxn), and 0.02 pg/ml (60 copies/rxn) were used as templates for the standard curve generated by real-time PCR analysis.

The samples were arranged in the order shown in Table 3. The four aliquot serum samples are in capillary positions 1-4. For samples A and B, Q-beta bacteriophage was added before the centrifugation step at 120,000×g (Q-beta before, QB-B). For samples C and D, Q-beta bacteriophage was added after the centrifugation step at 120,000×g (Q-beta after, QB-A).

TABLE 3

Real-time PCR sample arrangement

| Capillary Position | Sample |
|---|---|
| 1 | A (QB-B) |
| 2 | B (QB-A) |
| 3 | C (QB-B) |
| 4 | D(QB-A) |
| 5 | QB Plasmid 60000 copies |
| 6 | QB Plasmid 6000 copes |
| 7 | QB Plasmid 600 copies |
| 8 | QB Plasmid 60 copies |

Figure 1B:
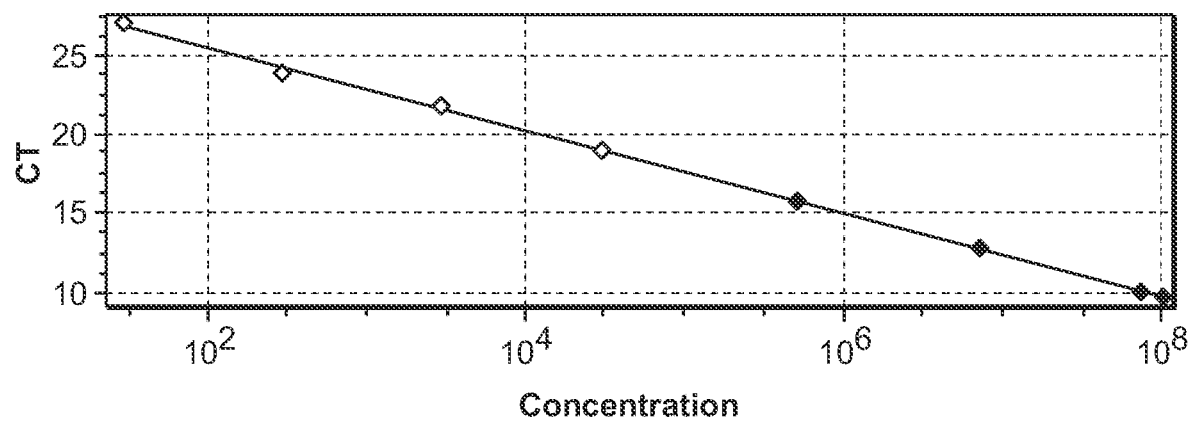
FIG. 1B is a standard curve used to plot the Ct values of Q-beta coat protein gene in serum samples in RT-PCR analysis. The X axis represents the concentration in copy numbers per reaction. The Y axis represents Ct values in RT-PCR analysis.

The amplification curves for all samples are shown in FIG. 1A. The Ct values and copy numbers were used to generate a standard curve for real-time PCR. As shown in FIG. 1B, extrapolation of the standard curve gives an estimate of the copy numbers of Q-beta coat protein gene in the four serum samples. The Ct values and the calculated copy number of the Q-beta coat protein gene from the real-time PCR are shown in Table 4. In the QB-B samples A and B, the Ct values were 15.71 and 12.64, respectively. In the QB-A samples C and D, the Ct values were 9.99 and 9.61, respectively. There appeared to be some loss of Q-beta coat protein gene copies during the step of centrifugation at 120,000×g as the Ct value was larger (the calculated copies/reaction was smaller) for QB-B than for QB-A samples.

The low Ct values in the real-time PCR assays indicate excellent recovery and amplification of the Q-beta bacteriophage coat genes using microvesicle RNA extraction methods, particularly for when the control particle was added after the microvesicle isolation step. Therefore, Q-beta bacteriophage can be used as an internal control for serum microvesicle RNA extraction and analysis.

TABLE 4

Real-time PCR results in serum samples

| No. | Sample | Type | Ct | Given Conc (copies/reaction) | Calc Conc (copies/reaction) | % Var |
|---|---|---|---|---|---|---|
| 1 | A (QB-B) | Unknown | 15.71 |  | 1,023,595 |  |
| 2 | B (QB-A) | Unknown | 9.99 |  | 149,139,538 |  |
| 3 | C (QB-B) | Unknown | 12.64 |  | 14,814,516 |  |

TABLE 4-continued

Real-time PCR results in serum samples

| No. | Sample | Type | Ct | Given Conc (copies/reaction) | Calc Conc (copies/reaction) | % Var |
|---|---|---|---|---|---|---|
| 4 | D (QB-A) | Unknown | 9.61 | | 208,057,863 | |
| 5 | QB Plasmid 60000 copies | Standard | 18.96 | 60,000 | 60,409 | 0.7% |
| 6 | QB Plasmid 6000 copies | Standard | 21.75 | 6,000 | 5,290 | 11.8% |
| 7 | QB Plasmid 600 copies | Standard | 23.99 | 600 | 756 | 26.0% |
| 8 | QB Plasmid 60 copies | Standard | 27.02 | 60 | 54 | 10.6% |

Example 2: Q-Beta Bacteriophage as an Internal Control for Urine RNA Analysis

In this example, Q-beta bacteriophage was utilized as an internal control for microvesicle and RNA extraction in urine samples. A urine sample was obtained from a normal, healthy human volunteer and divided into four 20 ml samples (Samples 1, 2, 3, and 4). Each sample was filtered through a 0.8 µm filter (Millipore) by addition to the filtration concentrator upper chamber.

The Q-beta bacteriophage (Attostar catalog No. BAC200) was diluted such that 500 and 50 copies of bacteriophage could be added to the urine samples as controls. 500 copies of Q-beta bacteriophage was added into samples 1 and 2. 50 copies of Q-beta bacteriophage was added into samples 3 and 4.

The concentrated samples containing microvesicles and Q-beta particles were then washed on the filter three times by adding 15 ml PBS, and centrifuging the filter at about 4,500×g for 5 minutes at room temperature. The particles retained on each filter membrane were then transferred to a new tube with containing 50 µl PBS. RNA was extracted from the particles using RNeasy Plus Micro Kit (Qiagen). First, 350 µl lysis buffer RLT plus 10 µl/ml beta-mercaptoethanol was added to each sample. The lysate was then transferred to DNA Eliminator spin column (Qiagen) in a 2 ml collection tube to obtain the filtrate. The RNA was precipitated by ethanol precipitation. The resulting RNA was washed in a RNeasy Micro spin column (Qiagen) once with 700 µl RWT buffer and then twice with 500 µl RPE buffer (Qiagen). The RNA was eluted in 16 µl nuclease-free $H_2O$.

The expression of the Q-beta coat protein gene expression levels were analyzed in the samples by RT-PCR. For that purpose, cDNA was generated from the extracted RNA by reverse transcription. Specifically, 12 µl of the extracted RNA was reverse transcribed t using a VILO™ kit (Invitrogen). The reverse transcription reaction mixture was prepared according to the following scheme (Table 5).

TABLE 5

Reverse transcription reaction mixture scheme.

| | (µl) × 1 reaction | ×4.4 |
|---|---|---|
| 5X VILO ™ Reaction Mix | 4 | 17.6 |
| 10X SuperScript ® Enzyme Mix | 2 | 8.8 |
| RNA (up to 2.5 µg) | 12 | — |
| Nuclease free water | 2 | 8.8 |
| Total volume | 20 | |

The reverse transcription was performed in a Veriti Thermal Cycler (Applied Biosystems) under the following conditions: 25° C. for 10 minutes, 42° C. for 70 minutes, 85° C. for 5 minutes, and was held in 4° C. before the reaction was stored at −20° C.

Multiplex real-time PCR was utilized to analyze the levels of Q-beta coat protein together with GAPDH, Albumin, and 18s rRNA. Each PCR sample contained 2 µl of cDNA. The primers-probe for Q-beta coat protein gene was from QB Primers-probe Quasar670-BHQ2 (Attostar catalog No. PP201). The primers for with GAPDH, Albumin, and 18s rRNA are from Life Technologies. The real-time PCR master mix was Taqman® Gene Expression Master from Life Technologies. The real-time PCR mixture was made according to the scheme in Table 6. The total reaction volume per reaction was 20 µl. The real-time PCR was performed under the following conditions: 95° C. for 10 minutes; 40 cycles of 95° C. for 10 seconds, 55° C. for 15 seconds, and 72° C. for 20 seconds.

TABLE 6

Reverse transcription reaction mixture scheme.

| Component | Volume (µL)/reaction |
|---|---|
| H2O | 5 |
| 10X QB Primers-probe Quasar670-BHQ2 | 2 |
| 20X Taqman ® Gene Expression Assay | 1 |
| 2X Taqman ® Gene Expression Master Mix | 10 |
| cDNA Sample volume | 2 |
| Final reaction Volume | 20 |

For the purpose of standardization, Q-beta plasmid DNA (Attostar catalog No. PLAS200) was added to each real-time PCR sample. The Q-beta plasmid DNA was diluted in water sequentially at 10 fold such that the Q-beta plasmid concentration was at 200 pg/ml, 20 pg/ml, 2 pg/ml, 0.2 pg/ml, and 0.02 pg/ml. The 0.02 pg/ml plasmid solution contains 12 copies of Q-beta plasmid in 2 µl. We used as templates in real-time PCR 2 µl diluted Q-beta plasmid at 200 pg/ml (115,000 copies/rxn), 20 pg/ml (11,500 copies/rxn), 2 pg/ml (1,150 copies/rxn), 0.2 pg/ml (115 copies/rxn), and 0.02 pg/ml (12 copies/rxn) as standards for real-time PCR.

The samples were arranged in the order shown in Table 7. The four urine samples as Sample IDs "F1 500-1", "F1 500-2", "F1 50-1", and "F1 50-2" were analyzed in capillary positions 2-5, 8-11, and 14-17. For samples F1 500-1 and F1 500-2, 500 copies of Q-beta bacteriophage were added in the urine sample. For samples F1 50-1 and F1 50-2, 50 copies of Q-beta bacteriophage was added in the urine samples. The multiplex PCR ID refers to which gene (GAPDH=G, Albumin=A, or 18s rRNA=18s) the Q-beta coat protein gene primers were multiplexed with. For example, G-Q-beta 500-1 refers to a multiplex PCR reaction comprising primers and probes for both GAPDH and Q-beta in sample ID F1 500-1. Similarly, A-Q-beta 500-1 refers to a multiplex PCR reaction comprising primers and probes for both Albumin and Q-beta in sample ID F1 500-1. Similarly, 18s-Q-beta 500-1 refers to a multiplex PCR reaction comprising primers and probes for both 18s rRNA and Q-beta in sample ID F1 500-1.

TABLE 7

Real-time PCR sample arrangement

| Capillary Position | Sample ID | Multiplex PCR ID |
|---|---|---|
| 1 | Negative RT | Negative RT |
| 2 | F1 500-1 | G-Q-beta 500-1 |
| 3 | F1 500-2 | G-Q-beta 500-2 |
| 4 | F1 50-1 | G-Q-beta 50-1 |
| 5 | F1 50-2 | G-Q-beta 50-2 |
| 6 | NT | NT |
| 7 | Negative RT | Negative RT |
| 8 | F1 500-1 | A-Q-beta 500-1 |
| 9 | F1 500-2 | A-Q-beta 500-2 |
| 10 | F1 50-1 | A-Q-beta 50-1 |
| 11 | F1 50-2 | A-Q-beta 50-2 |
| 12 | NT | NT |
| 13 | Negative RT | Negative RT |
| 14 | F1 500-1 | 18s-Q-beta 500-1 |
| 15 | F1 500-2 | 18s-Q-beta 500-2 |

TABLE 7-continued

Real-time PCR sample arrangement

| Capillary Position | Sample ID | Multiplex PCR ID |
|---|---|---|
| 16 | F1 50-1 | 18s Q-beta 50-1 |
| 17 | F1 50-2 | 18s-Q-beta 50-2 |
| 18 | NT | NT |
| 19 | QB Plasmid 115000 | QB Plasmid 115000 |
| 20 | QB Plasmid 11500 | QB Plasmid 11500 |
| 21 | QB Plasmid 1150 | QB Plasmid 1150 |
| 22 | QB Plasmid 115 | QB Plasmid 115 |
| 23 | QB Plasmid 12 | QB Plasmid 12 |

Figure 2A:
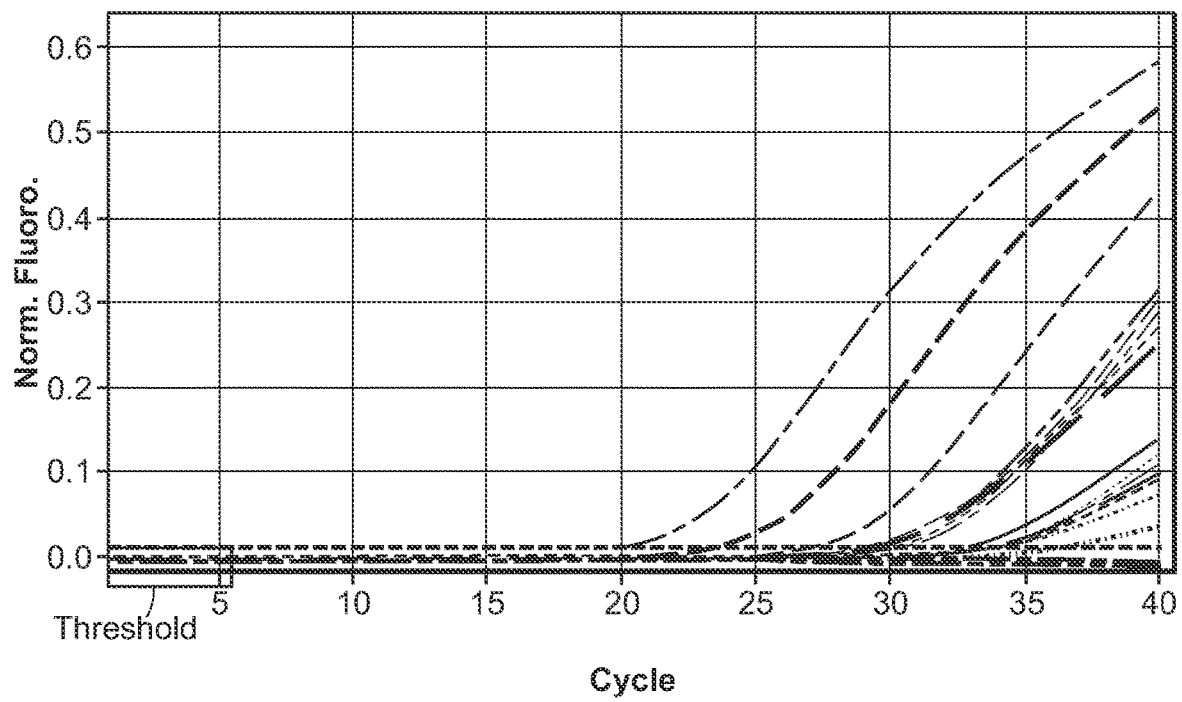
FIG. 2A is a plot of amplification curves in RT-PCR analysis of Q-beta coat protein gene in urine samples. The X axis represents the number of PCR amplification cycles. The Y axis represents the normalized fluorescence, which indicates the magnitude of the signal generated by the given set of PCR conditions.
Figure 2B:
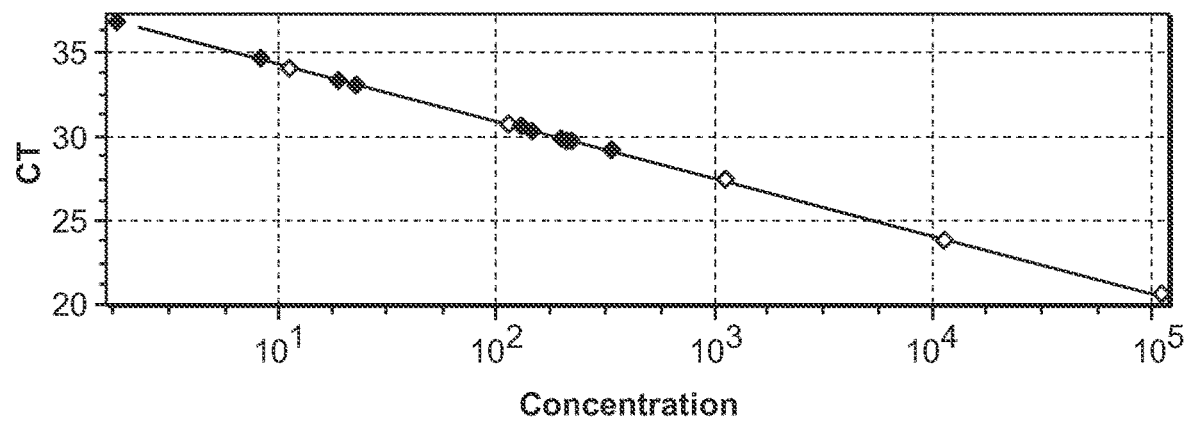
FIG. 2B is a standard curve used to plot the Ct values of Q-beta coat protein gene in urine samples in RT-PCR analysis. The X axis represents the concentration in copy numbers per reaction. The Y axis represents Ct values in RT-PCR analysis.

The Q-beta coat protein gene amplification curves for all samples are shown in FIG. 2A. The Ct values and copy numbers of the Q-beta plasmid standards were used to generate a standard curve for real-time PCR. As shown in FIG. 1B, extrapolation of the standard curve could give an estimate of the copy numbers of Q-beta coat protein gene in the four samples. The Ct values and the calculated copy number of the Q-beta coat protein gene from the real-time PCR are shown in Table 8. In the urine samples with 500 copies of Q-beta bacteriophage added, the Ct values were about 29.03-30.46 with calculated copy number about 145-345. In the samples with 50 copies of Q-beta bacteriophage added, the Ct values were within the range of 33.03-36.73 with calculated copy number within the range of 2-23 copies. The calculated copy numbers were close to the copy number added, suggesting that bacteriophage RNA was sufficiently recovered and therefore could be used as a control to determine the quality of the microvesicle purification process.

TABLE 8

Real-time PCR results for Q-beta coat protein gene in urine samples

| Capillary Position | Sample ID | Type | Ct | Given Conc (copies/μl) | Calc Conc (copies/μl) | % Var |
|---|---|---|---|---|---|---|
| 1 | Negative RT | Unknown | | | | |
| 2 | F1 500-1 | Unknown | 29.71 | | 217.4 | |
| 3 | F1 500-2 | Unknown | 30.29 | | 146.7 | |
| 4 | F1 50-1 | Unknown | 33.03 | | 22.8 | |
| 5 | F1 50-2 | Unknown | 34.50 | | 8.4 | |
| 6 | NT | Unknown | | | | |
| 7 | Negative RT | Unknown | | | | |
| 8 | F1 500-1 | Unknown | 29.84 | | 199.1 | |
| 9 | F1 500-2 | Unknown | 30.46 | | 130.5 | |
| 10 | F1 50-1 | Unknown | 36.73 | | 1.8 | |
| 11 | F1 50-2 | Unknown | 34.14 | | 10.7 | |
| 12 | NT | Unknown | | | | |
| 13 | Negative RT | Unknown | | | | |
| 14 | F1 500-1 | Unknown | 29.03 | | 344.6 | |
| 15 | F1 500-2 | Unknown | 29.65 | | 226.2 | |
| 16 | F1 50-1 | Unknown | 33.30 | | 19.0 | |
| 17 | F1 50-2 | Unknown | 34.08 | | 11.2 | |
| 18 | NT | Unknown | | | | |
| 19 | QB Plasmid | Standard | 20.53 | 115,000.0 | 111,716.1 | 2.9% |
| 20 | QB Plasmid | Standard | 23.77 | 11,500.0 | 12,333.9 | 7.3% |
| 21 | QB Plasmid | Standard | 27.34 | 1,150.0 | 1,089.1 | 5.3% |
| 22 | QB Plasmid | Standard | 30.63 | 115.0 | 116.7 | 1.5% |
| 23 | QB Plasmid | Standard | 34.04 | 11.5 | 11.5 | 0.1% |

Figure 3A:
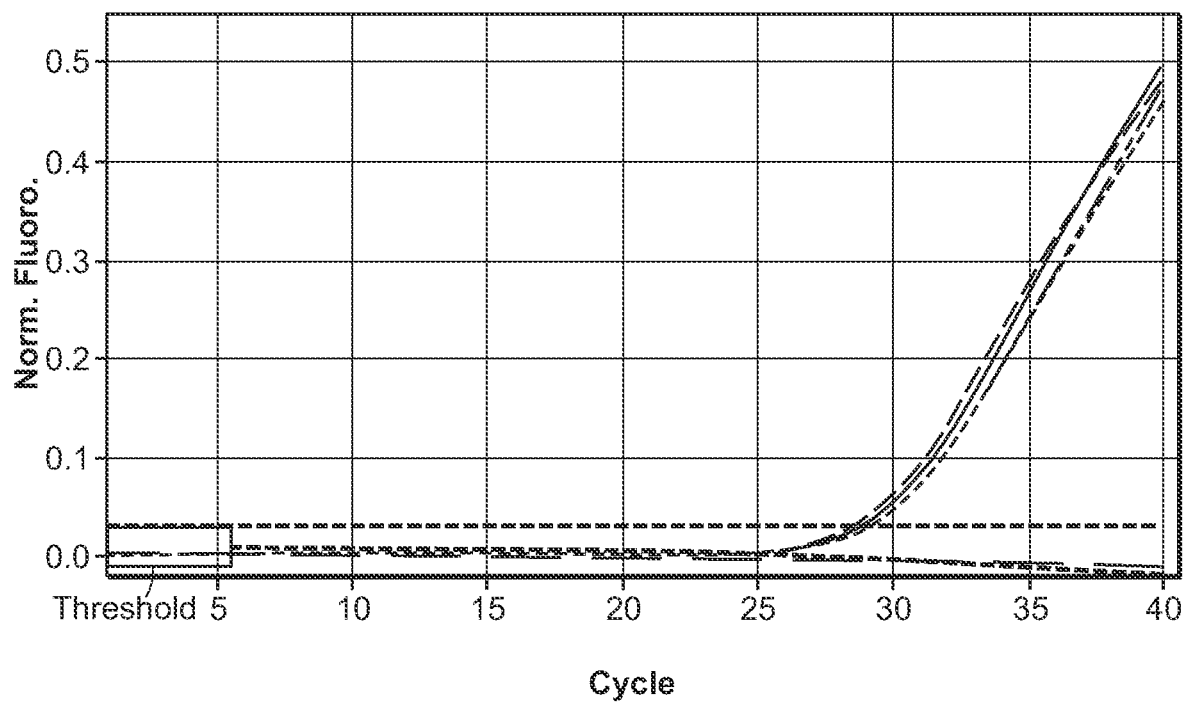
FIG. 3A is a plot of amplification curves in RT-PCR analysis of albumin gene and 18s rRNA in urine samples. The X axis represents the number of PCR amplification cycles. The Y axis represents the normalized fluorescence, which indicates the magnitude of the signal generated by the given set of PCR conditions.
Figure 3B:
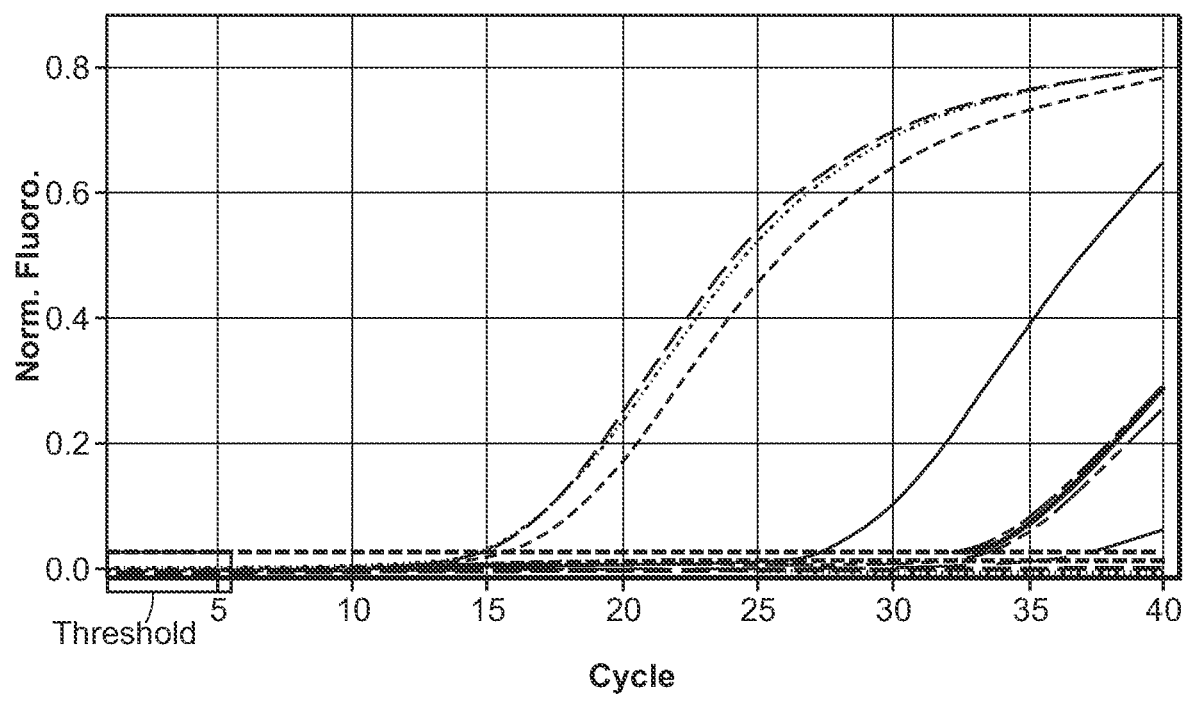
FIG. 3B is a plot of amplification curves in RT-PCR analysis of GAPDH gene in urine samples. The X axis represents the number of PCR amplification cycles. The Y axis represents the normalized fluorescence, which indicates the magnitude of the signal generated by the given set of PCR conditions.

The GAPDH gene amplification curves for the four urine samples are shown in FIG. 3A. The Albumin and 18S rRNA amplification curves for the four urine samples are shown in FIG. 3B. Extrapolation of the standard curve gives an estimate of the copy numbers of Q-beta coat progein gene as detailed above. Similar extrapolation allows the calculation of the estimated copy numbers of GAPDH, Albumin, and 18S rRNA. The Ct values and the calculated copy numbers of GAPDH, Albumin and 18S rRNA from the real-time PCR analysis are shown in Table 9.

These data suggest that there was no obvious interference from the primers and probes for the Q-beta coat protein gene in the duplexed real-time PCR reactions for each of the three genes tested. First, the Ct numbers for GAPDH, 18S rRNA and Albumin were all within the Ct range expected for the urine microvesicles. In addition, the Ct values for each of the three genes were reproducible between the replicate samples (500 copies of bacteriophage and 50 copies of bacteriophage). For example, the Ct range for GAPDH was 28.60-29.39.

Therefore, in the urine microvesicle isolation methods, the Q-beta bacteriophage RNA could be recovered sufficiently and could be used as an internal control with confidence. Further, the primers and probe for Q-beta bacteriophage coat protein gene did not appear to interfere with the gene amplification in duplex tests. Together with the data shown in Example 1, this disclosure demonstrates that Q-beta bacteriophage can be used as an internal control in the microvesicle RNA analysis both in urine and in serum samples.

TABLE 9

Real-time PCR results for GAPDH, Albumin and 18S rRNA in urine samples

| Capillary Position | Multiplex PCR ID | Ct |
|---|---|---|
| 1 | Negative RT | |
| 2 | G-Q-beta 500-1 | 28.60 |
| 3 | G-Q-beta 500-2 | 29.27 |
| 4 | G-Q-beta 50-1 | 28.97 |
| 5 | G-Q-beta 50-2 | 29.39 |
| 6 | NT | |
| 7 | Negative RT | |
| 8 | A-Q-beta 500-1 | 32.76 |
| 9 | A-Q-beta 500-2 | 37.32 |
| 10 | A-Q-beta 50-1 | 33.79 |
| 11 | A-Q-beta 50-2 | 33.36 |
| 12 | NT | |
| 13 | Negative RT | 27.51 |
| 14 | 18S-Q-beta 500-1 | 14.73 |
| 15 | 18S-Q-beta 500-2 | 14.99 |
| 16 | 18S-Q-beta 50-1 | 14.84 |
| 17 | 18S-Q-beta 50-2 | 15.93 |
| 18 | NT | |

Example 3: Using Q-Beta Control Particles in Assessing Patient Samples

Urine samples from a patient cohort was used to identify biomarkers useful for detecting prostate cancer from nucleic acids extracted from the urine-derived microvesicles. Urine samples were collected and filtered through a 0.8 um filter to separate cells and other cell debris from the microvesicles. Q-beta control particles were added to the samples at a known quantity (e.g., 100 copies) to the urine sample. The microvesicle fraction was then additionally processed, for example, through a filtration concentrator. The retentate was washed, at least once (e.g., twice), and re-spun in the filter concentrator. RNase inhibitor was added to the retentate located in the upper chamber of the filter concentrator, and incubated at room temperature for 2-3 minutes. Lysis buffer was added to the sample directly and incubated for 1 minute at room temperature. The lysate was then transferred to another container to continue with nucleic acid extraction using methods well known in the art and conditions suitable to yield high quality RNA. Nucleic acid extraction was performed, for example, utilizing columns that separate and retain the nucleic acids, specifically RNA, from the lysate. The extracted RNA is the eluted from the column. The extracted RNA contains RNA from the urine-derived microvesicles as well as the Q-beta particles, and is reverse transcribed to cDNA for quantitative real-time PCR analysis of the Q-beta coat protein gene, a biomarker, such as PCA3, and a reference gene, such as KLK3.

Figure 4:
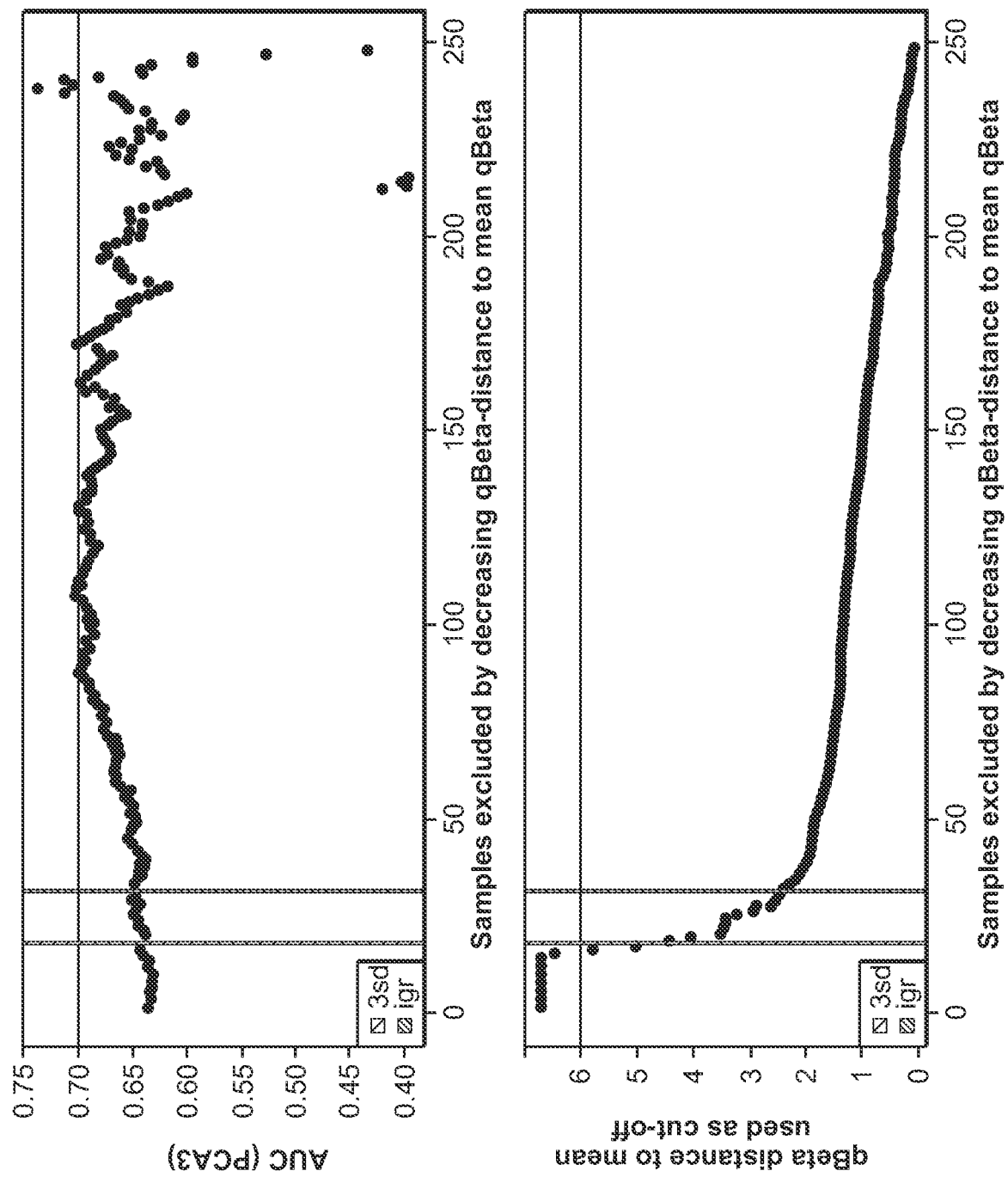
FIG. 4 is two graphs correlating PCA3 AUC values in samples by successively removing samples with high Q-beta Cts. In the top graph, the Y axis represents AUC values and the X axis represents the samples excluded by decreasing Q-beta-distance to mean Q-beta (standard deviation). In the bottom graph, the Y axis represents the Q-beta distance to mean (standard deviation) used as cutoff and the X axis represents the samples excluded by decreasing Q-beta-distance to mean Q-beta (standard deviation).

The quantity of recovered Q-beta particles was calculated for each sample (Ct value). The mean Ct values for recovered Q-beta particles for the entire cohort was calculated. The standard deviation of Ct values for the recovered Q-beta particles for the entire cohort was also calculated. FIG. 4 shows the results of the experiment and demonstrates that the successive removal of samples in which the quantification of the Q-beta particles recovered resulted in high Ct values. Samples that did not yield a qPCR signal (or Ct value), or samples that deviated more than 3 times the standard deviation from the mean of all the Ct values were considered outliers and were excluded from further analysis. As shown in FIG. 4, when the outliers were removed, the diagnostic accuracy of the biomarker PCA3 increased, as shown by the increase in the AUC (Area Under the Curve) values.

While the present invention has been disclosed with reference to certain embodiments, numerous modifications, alterations, and changes to the described embodiments are possible without departing from the full scope of the invention, as described in the appended specification and claims.

What is claimed is:

1. A method comprising:
   (a) forming a mixture by adding a known quantity of control particles to a biological sample comprising microvesicles, wherein the control particles are Q-beta bacteriophage particles, wherein the Q-beta bacteriophage particles comprise a known copy number of a control nucleic acid, and wherein the microvesicles comprise nucleic acids;
   (b) isolating a fraction comprising the microvesicles and the control particles from the mixture;
   (c) extracting nucleic acids from the fraction comprising the microvesicles and the control particles, thereby producing extracted nucleic acids;
   (d) measuring the amount of the control nucleic acid in the extracted nucleic acids of step (c) by a quantitative polymerase chain reaction (PCR) using specific primers that hybridize to the control nucleic acid;
   (e) determining the copy number of the control nucleic acid in the extracted nucleic acids of step (c) by comparing the amount of the control nucleic acid measured in step (d) to a standard curve generated using known different concentrations of the control nucleic acid and known different copy numbers of the control nucleic acid;
   (f) determining the amount of the control particles that are present in the fraction from step (b) based on the copy number of the control nucleic acid in the extracted nucleic acids determined in step (e); and
   (g) subjecting the extracted nucleic acids from step (c) to further analysis if the amount of the control particles determined in step (f) is within a predetermined range of values.

2. The method of claim 1, wherein the biological sample is a bodily fluid sample.

3. The method of claim 2 wherein the bodily fluid sample is urine sample, blood sample, cerebrospinal fluid sample, plasma sample or serum sample.

4. The method of claim 3, wherein the bodily fluid sample is a urine sample.

5. The method of claim 3, wherein the bodily fluid sample is a blood sample.

6. The method of claim 3, wherein the bodily fluid sample is a plasma sample.

7. The method of claim 1, wherein the control nucleic acid comprises RNA or DNA.

8. The method of claim 1, wherein the control nucleic acid comprises a Q-beta coat protein gene.

9. The method of claim 1, wherein the fraction comprising the microvesicles and the control particles is isolated by differential centrifugation, gel permeation chromatography, anion exchange chromatography, a sucrose density gradient, organelle electrophoresis or any combination thereof.

10. The method of claim 1, wherein the control nucleic acid is RNA and the quantitative PCR is a reverse transcription quantitative PCR.

* * * * *